(12) United States Patent
Carpentier et al.

(10) Patent No.: US 10,857,227 B2
(45) Date of Patent: Dec. 8, 2020

(54) IMMUNOSTIMULATORY COMPOSITIONS

(71) Applicants: ASSISTANCE PUBLIQUE-HOPITAUX DE PARIS, Paris (FR); UNIVERSITÉ PARIS 13, Villetaneuse (FR)

(72) Inventors: Antoine Carpentier, Paris (FR); Claire Banissi, Vincennes (FR)

(73) Assignees: ASSISTANCE PUBLIQUE—HOSPITAUX DE PARIS, Paris (FR); UNIVERSITÉ PARIS 13, Villetaneuse (FR)

( * ) Notice: Subject to any disclaimer, the term of this patent is extended or adjusted under 35 U.S.C. 154(b) by 114 days.

(21) Appl. No.: 15/778,929

(22) PCT Filed: Nov. 25, 2016

(86) PCT No.: PCT/EP2016/078794
§ 371 (c)(1),
(2) Date: May 24, 2018

(87) PCT Pub. No.: WO2017/089529
PCT Pub. Date: Jun. 1, 2017

(65) Prior Publication Data
US 2018/0333483 A1 Nov. 22, 2018

(30) Foreign Application Priority Data
Nov. 27, 2015 (EP) .................................... 15306887

(51) Int. Cl.
*A61K 39/385* (2006.01)
*A61K 39/00* (2006.01)

(52) U.S. Cl.
CPC .. *A61K 39/385* (2013.01); *A61K 2039/55511* (2013.01); *A61K 2039/55516* (2013.01); *A61K 2039/572* (2013.01); *A61K 2039/575* (2013.01); *A61K 2039/6031* (2013.01); *A61K 2039/6093* (2013.01)

(58) Field of Classification Search
None
See application file for complete search history.

(56) References Cited

U.S. PATENT DOCUMENTS

| 2004/0057958 A1 | 3/2004 | Waggoner et al. |
| 2006/0024328 A1 | 2/2006 | Pasco et al. |
| 2012/0237605 A1 | 9/2012 | Messersmith et al. |

FOREIGN PATENT DOCUMENTS

| JP | H05503308 A | 6/1993 |
| JP | 2014510104 A | 4/2014 |
| WO | WO-92/07580 A1 | 5/1992 |
| WO | WO-2000/040262 A1 | 7/2000 |
| WO | WO-2008/057529 A2 | 5/2008 |
| WO | WO-2012/129047 A1 | 9/2012 |

OTHER PUBLICATIONS

Mon et al, Brain Research 1988; 451:403-407. (Year: 1988).*
Nosanchuk et al J Immunol 1998; 160:6026-6031. (Year: 1998).*
Xiao-Ming Liu et al., "Maintenance of immune hyporesponsiveness to melanosomal proteins by DHICA-mediated antioxidation: Possible implications for autoimmune vitiligo," Free Radical Biology & Medicine, vol. 50, 2011, pp. 1177-1185.
James A. MacKintosh, "The Antimicrobial Properties of Melanocytes, Melanosomes and Melanin and the Evolution of Black Skin," J. theor. Biol., vol. 211, 2001, pp. 101-113.
Charles Maisonneuve et al., "Unleashing the potential of NOD- and Toll-like agonists as vaccine adjuvants," PNAS, vol. 111, No. 34, 2014, pp. 12294-12299.
Hiroshi Mitsui et al., "Polyarginine-Mediated Protein Delivery to Dendritic Cells Presents Antigen More Efficiently onto MHC Class I and Class II and Elicits Superior Antitumor Immunity," Journal of Investigative Dermatology, vol. 126, 2006, pp. 1804-1812.
Mohagheghpour N et al., "Synthetic melanin suppresses production of proinflammatory cytokines," Cell Immunol., vol. 199, No. 1, 2000, p. 25—Abstract.
Yoichi Moroi et al., "Induction of cellular immunity by immunization with novel hybrid peptides complexed to heat shock protein 70," PNAS, vol. 97, No. 7, 2000, pp. 3485-3490.
Mark J. Newman et al., "Development of adjuvant-active nonionic block copolymers," Advanced Drug Delivery Reviews, vol. 32, 1998, pp. 199-223.
Rodrigo Pacheco et al., "The dopaminergic system in autoimmune diseases," Frontiers in Immunology, vol. 5, Article 117, 2014, pp. 1-17.
Anna Palumbo et al., Effect of metal ions on the rearrangements of dopachrome, Biochimica et Biophysica Acta, vol. 925, 1987, pp. 203-209.
Anna Palumbo et al., "Comparative action of dopachrome tautomerase and metal ions on the rearrangement of dopachrome," Biochimica et Biophysica Acta, vol. 1115, 1991, pp. 1-5.
Anastassios C. Papageorgiou et al., "Superantigens as immunomodulators: recent structural insights," Structure, vol. 5, 1997, pp. 991-996.
Steven G. Reed et al., "New horizons in adjuvants for vaccine development," Trends in Immunology, vol. 30, No. 1, 2008, pp. 23-32.
A. L. Rosas et al., "Activation of the Alternative Complement Pathway by Fungal Melanins," Clinical and Diagnostic Laboratory Immunology, vol. 9, No. 1, 2002, pp. 144-148.
Kristen Sadler et al., "Peptide dendrimers: applications and synthesis," Reviews in Molecular Biotechnology, vol. 90, 2002, pp. 195-229.
Chandrani Sarkar et al., "The immunoregulatory role of dopamine: an update," NIH Public Access, vol. 24, No. 4, 2010, pp. 1-8.
Julia Scheiermann et al., "Clinical evaluation of CpG oligonucleotides as adjuvants for vaccines targeting infectious diseases and cancer," Vaccine, vol. 32, 2014, pp. 6377-6389.

(Continued)

*Primary Examiner* — Padmavathi Baskar
(74) *Attorney, Agent, or Firm* — Polsinelli PC

(57) ABSTRACT

The invention relates to the use of melanin, complexed with an antigen, as a immunostimulatory composition.

17 Claims, 9 Drawing Sheets
Specification includes a Sequence Listing.

(56) References Cited

OTHER PUBLICATIONS

Carola Schellack et al., "IC31, a novel adjuvant signaling via TLR9, induces potent cellular and humoral immune responses," Vaccine, vol. 24, 2006, pp. 5461-5472.
Claire-Anne Siegrist, "Vaccine immunology," General aspects of vaccination, Section 1, 2007, pp. 17-36.
Andrzej Slominski et al., "Melanin Pigmentation in Mammalian Skin and Its Hormonal Regulation," American Physiological Society, vol. 84, 2004, pp. 1155-1228.
Mark S. Sonders et al., "Multiple Ionic Conductances of the Human Dopamine Transporter: The Actions of Dopamine and Psychostimulants," the Journal of Neuroscience, vol. 17, No. 3, 1997, pp. 960-974.
Kim Langfelder et al., "Biosynthesis of fungal melanins and their importance for human pathogenic fungi," Fungal Genetics and Biology, vol. 38, 2003, pp. 143-158.
Bruce P. Lee et al., "Synthesis and Gelation of Dopa-Modified Poly(ethylene glycol) Hydrogels," Biomacromolecules, vol. 3, 2002, pp. 1038-1047.
Haeshin Lee et al., "Facile Conjugation of Biomolecules onto Surfaces via Mussel Adhesive Protein Inspired Coatings," NIH Public Access, vol. 21, No. 4, 2009, pp. 431-434.
International Search Report and Written Opinion dated Mar. 17, 2017 in corresponding PCT Application No. PCT/EP2016/078794.
Ruth Aron et al., "Studies on the chemical basis of the antigenicity of proteins. 2. Antigenic specificity of polytyrosyl gelatins," Biochemical Journal, vol. 75, No. 1, 1960, pp. 103-109.
M. Sela et al., "Studies on the chemical basis of the antigenicity of proteins. 1. Antigenicity of Polypeptidyl Gelatins," Biochemical Journal, vol. 75, No. 1, 1960, pp. 91-102.
Takami Akagi et al., "Biodegradable Nanoparticles as Vaccine Adjuvants and Delivery Systems: Regulation of Immune Responses by Nanoparticle-Based Vaccine," Adv. Polym. Sci., vol. 247, 2012, pp. 31-64.
Yoshio Fujita et al., "Current status of multiple antigen-presenting peptide vaccine systems: Application of organic and inorganic nanoparticles," Chemistry Central Journal, vol. 5, No. 1, 2011, pp. 1-8.
Jiwei Cui et al., "Immobilization and Intracellular Delivery of an Anticancer Drug Using Mussel-Inspired Polydopamine Capsules," American Chemical Society Publications, vol. 13, No. 8, 2012, pp. 2225-2228.
Xinyu Cui et al., "Polydopamine used as Hollow Capsule and Core-Shell Structures for Multiple Applications," Nano, vol. 10, No. 5, 2015, pp. 1530003-1-1530003-23.
Haeshin Lee et al., "Facile Conjugation of Biomolecules onto Surfaces via Mussel Adhesive Protein Inspired Coatings," Advanced Materials, vol. 21, No. 4, 2009, pp. 431-434.
Joonyoung Park et al., "Polydopamine-Based Simple and Versatile Surface Modification of Polymeric Nano Drug Carriers," ACS Nano, vol. 8, No. 4, 2014, pp. 3347-3356.
Qi Liu et al., "Pathogen-Mimicking Polymeric Nanoparticles based on Dopamine Polymerization as Vaccines Adjuvants Induce Robust Humoral and Cellular Immune Responses," Small, 2016, pp. 1-14.
Hegedus, Zoltan L., "The probable involvement of soluble and deposited melanins, their intermediates and the reactive oxygen side-products in human diseases and aging", Toxicology, vol. 145, 2000; pp. 85-101.
Mary Struthers et al., Synthesis and immunological activities of novel agonists of toll-like receptor 9, Cellular Immunology, vol. 263, 2010, pp. 105-113.
Manickam Sugumaran et al., "Nonenzymatic transformations of enzymatically generated N-acetyldopamine quinone and isomeric dihydrocaffeiyl methyl amide quinone," FEBS Letters, vol. 255, No. 2, 1989, pp. 345-349.
James P. Tam, "Synthetic peptide vaccine design: Synthesis and properties of a high-density multiple antigenic peptide system," Proc. Natl. Acad. Sci. USA, vol. 85, 1988, pp. 5409-5413.

Maiko Taneichi et al., "Antigen Chemically Coupled to the Surface of Liposomes are Cross-Presented to CD8+T Cells and Induce Potent Antitumor Immunity," the Journal of Immunology, vol. 177, 2006, pp. 2324-2330.
Alain C. Tissot et al., "Versatile Virus-Like Particle Carrier for Epitope Based Vaccines," PLoS One, vol. 5, No. 3, 2010, pp. 1-8.
Lumi Viljakainen, "Evolutionary genetics of insect innate immunity," Briefings in Functional Genomics, 2015, pp. 1-6.
Michael Waisberg et al., "Testing in Mice the Hypothesis That Melanin is Protective in Malaria Infections," PLoS One, vol. 7, No. 1, 2012, pp. 1-9.
Jing Wang et al., "Co-polypeptides of 3,4-dihydroxyphenylalanine and L-lysine to mimic marine adhesive protein," Science Direct, Biomaterials, vol. 28, 2007, pp. 3456-3468.
Houliang Wei et al., "Stability of polydopamine and poly(DOPA) melanin-like films on the surface of polymer membranes under strongly acidic and alkaline conditions," Colloids and Surfaces B: Biointerfaces, vol. 110, 2013, pp. 22-28.
Mehfuz Zaman et al., "Nanovaccines and their mode of action," Methods, vol. 60, 2013, pp. 226-231.
Liang Zhao et al., "Nanoparticle vaccines," Vaccine, vol. 32, 2014, pp. 327-337.
Xinmei Zhu et al., "Toll like receptor-3 ligand poly-ICLC promotes the efficacy of peripheral vaccinations with tumor antigen-derived peptide epitopes in murine CNS tumor models," Journal of Translational Medicine, vol. 5, No. 10, 2007, pp. 1-15.
Svend Olav Andersen, "Insect cuticular sclerotization: A review," Insect Biochemistry and Molecular Biology, vol. 40, 2010, pp. 166-178.
Fazren Azmi et al., "Recent progress in adjuvant discovery for peptide-based subunit vaccines," Human Vaccines & Immunotherapeutics, vol. 10, No. 3, 2014, pp. 778-796.
Vincent Ball et al., "Kinetics of polydopamine film deposition as a function of pH and dopamine concentration: Insights in the polydopamine deposition mechanism," Journal of Colloid and Interface Science, vol. 386, 2012, pp. 366-372.
Pawel Bodera, "Immunostimulatory Oligonucleotides," Recent Patents on Inflammation & Allergy Drug Discovery, vol. 5, 2011, pp. 87-93.
Azam Bolhassani et al., "Improvement of different vaccine delivery systems for cancer therapy," Molecular Cancer, vol. 10, No. 3, 2011, pp. 1-20.
Nalini S. Bora et al., "Induction With Melanin-Associated Antigen From the Iris and Ciliary Body," Investigative Ophthalmology & Visual Science, vol. 36, No. 6, 1995, pp. 1056-1066.
Silvia B. Boscardin et al., "Antigen targeting to dendritic cells elicits long-lived T cell help for antibody responses," the Journal of Experimental Medicine, vol. 203, No. 3, 2006, pp. 599-606.
Broekhuyse RM et al., "Experimental autoimmune anterior uveitis (EAAU). II. Dose-dependent induction and adoptive transfer using a melanin-bound antigen of the retinal pigment epithelium." Exp Rye Res., vol. 55, No. 3, 1992, p. 401—Abstract.
Casadevall A et al., "Melanin and virulence in Cryptococcus neoformans," Curr Opin Microbiol., vol. 3, No. 4, 2000, p. 354—Abstract.
Marina Caskey et al., "Synthetic double-stranded RNA induces innate immune responses similar to a live viral vaccine in humans," the Journal of Experimental Medicine, vol. 208, No. 12, 2011, pp. 2357-2366.
Joao Conniot et al., "Cancer immunotherapy: nanodelivery approaches for immune cell targeting and tracking," Frontiers in Chemistry, vol. 2, Article 105, 2014, pp. 1-27.
Graeme Eisenhofer et al., "Tyrosinase: a developmentally specific major determinant of peripheral dopamine," the FASEB Journal, vol. 17, 2003, pp. 1248-1255.
Ioannis Eleftherianos et al., "Role and Importance of Phenoloxidase in Insect Hemostasis," Journal of Innate Immunity, vol. 3, 2011, pp. 28-33.
Camilla Foged et al., "License to kill: Formulation requirements for optimal priming of CD8+ CTL responses with particulate vaccine delivery systems," European Journal of Pharmaceutical Sciences, vol. 45, 2012, pp. 482-491.

(56) References Cited

OTHER PUBLICATIONS

Yoshio Fujita et al., "Current status of multiple antigen-presenting peptide vaccine systems: Application of organic and inorganic nanoparticles," Journal Chemistry Central, vol. 5, 2011, pp. 1-8.
Murat Guvendiren et al., "Adhesion of DOPA-Functionalized Model Membranes to Hard and Soft Surfaces," NIH Public Access, vol. 85, No. 9, 2009, pp. 631-645.
Annina M. Hafner et al., "Particulate formulations for the delivery of poly(I:C) as vaccine adjuvant," Advanced Drug Delivery Reviews, vol. 65, 2013, pp. 1386-1399.
Shosuke Ito et al., "Isolation of Oligomers of 5,6-Dihydroxyindole-2-carboxylic Acid from the Eye of the Catfish," Biochemistry Journal, vol. 143, 1974, pp. 207-217.
Dennis M. Klinman et al., "CpG oligonucleotides as adjuvants for vaccines targeting infectious diseases," Advanced Drug Delivery Reviews, vol. 61, 2009, pp. 248-255.
Kouji Kobiyama et al., "Nonagonistic Dectin-1 ligand transforms CpG into a multitask nanoparticulate TLR9 agonist," PNAS, vol. 111, No. 8, 2014, pp. 3086-3091.
R. M. Broekhuyse et al., "Experimental Autoimmune Posterior Uveitis Accompanied by Epitheloid Cell Accumulations (EAUP). A New Type of Experimental Ocular Disease Induced by Immunization with PEP-65, a Pigment Epithelial Polypeptide Preparation," Exp. Eye Res., vol. 55, 1992, pp. 819-829.
Hyo-Eun Jang et al., "Polydopamine-Coated Porous Microspheres Conjugated with Immune Stimulators for Enhanced Cytokine Induction in Macrophages," Macromolecular Journals, 2016, pp. 1-8.
Indu Mani et al., "Interaction of Melanin with Proteins—the Importance of an Acidic Intramelanosomal pH," Pigment Cell Res., vol. 14, 2001, pp. 170-179 XP009186796.
Vasyl M. Sava et al., "A novel melanin-like pigment derived from black tea leaves with immune-stimulating activity," Food Research International, vol. 34, 2001; pp. 337-343.

\* cited by examiner

IMMUNOSTIMULATORY COMPOSITIONS

CROSS-REFERENCE TO RELATED APPLICATIONS

This application is a national stage application (under 35 U.S.C. § 371) of PCT/EP2016/078794, filed Nov. 25, 2016, which claims benefit of European Application No. 15306887.9, filed Nov. 27, 2015, which are incorporated herein by reference in their entireties.

The invention is in the field of immunology, in particular in the field of adjuvants, i.e. elements that potentiate the immunogenic property of antigens, and is useful in particular in the field of vaccines, whether prophylactic or therapeutic.

Historical vaccines were based on live attenuated pathogens, whole inactivated organisms, or modified toxins. To limit potential side-effects, recent developments have focused on subunit vaccines which are generally composed of 30-60 amino acids, but can be limited to one epitope as short as 8 amino acids. The use of a small portion of an antigen limits the risk of potential cross-reactivity by focusing the immune response against the desired portion of an antigen. However, subunit vaccines, and especially peptide subunit vaccines, are often poorly immunogenic, due to the lack of pathogen-derived molecules to act as danger signals. Subunit vaccines thus require additional adjuvants to be effective (Fujita et al, Chem Cent J. 2011; 5(1):48; Azmi et al, Hum Vaccin Immunother. 2014; 10(3):778-96).

The mechanisms by which adjuvants exert their immune-enhancing effects are various (Siegrist 2007, Vaccines, Plotkin, Orenstein & Offit, Elsevier; Azmi et al 2014, op. cit.), and can rely, among others, on the following activities:

Presentation of the antigens to the immune system in an optimal manner; for example by translocation of antigens to the lymph nodes, by providing physical protection to antigens against degradation and/or a depot effect which grants the antigen a prolonged delivery, or by increasing antigen uptake within immune cells.

Activation the immune system; for example by activating pattern recognition receptors (PRRs) expressed on or within immune cells. Pattern recognition receptors (PRRs) of the innate immune system recognize conserved pathogen-associated molecular patterns and danger associated molecular patterns. Several PRRs have been identified, such as Toll-like receptors (TLRs), nucleotide-binding and oligomerization domain (NOD)-like receptors (NLRs), Retinoic-acid inducible gene (RIG)-like receptors (RLRs), DNA receptors, scavenger receptors, and C-type lectin receptors (CLRs) (Siegrist 2007 op. cit.; Conniot et al, Front Chem 2014; 2:105). Activation of PRRs results in the production of proinflammatory cytokines, but also activates antigen-presenting cells (APCs) such as dendritic cells (DCs) and macrophages to trigger an adaptive immune response (Maisonneuve et al, Proc Natl Acad Sci USA. 2014; 111(34):12294-9).

Some adjuvants activate either the antibody secretion by B-lymphocytes (humoral response), or the cytotoxic T lymphocytes (CTLs; also called CD8 T cells) response (cellular response), or both. B-lymphocytes recognize longer peptides starting at around 15 amino acids, presented on the surface of an antigen presenting cell (APC) by major histocompatibility complex (MHC) class II molecules. Cytotoxic T lymphocytes recognize short peptides of eight to ten amino acid residues, presented on the surface of an APC, or a target cell, by MHC class I molecules. The main processing pathway for MHC class I presentation involves degradation of cytosolic proteins. In some cases, extracellular soluble antigens or peptides, usually presented by MHC class II, are presented by the MHC class I, a process called cross-presentation (Foged et al., Eur J Pharm Sci. 2012 Mar. 12; 45(4):482-91). Licensing of cross-presentation by DC's can be initiated by CD4+ T-cell (CD40:CD40L ligation) or, in a CD4+ T-cell independent way, through ligation of innate PPRs such as the TLRs (mainly TLR3, TLR7/8 or TLR9) (Foged et al., op. cit.). Both cellular and humoral immune responses also require T-helper cells (TH-cells; also called CD4 T cells) to activate antigen presenting cell (the so called "second signal"). Therefore, vaccine components usually contain at least two antigenic epitopes: the target antigen that elicits an antigen-specific B cell or CTL response, and a TH epitope. Given the large number of polymorphisms in MHC class II genes in the population, some 'universal' TH epitopes binding a large number of MHC class II have been designed to be included in vaccines (P25, ptt-30, PADRE,). TH-cells are further subdivided into lineages (Th1, Th2, Th17, . . . ) according to their cytokine profiles and their ability to modulate B and cytotoxic CD8 response. Adjuvants can bias the immune responses towards Th1 or Th2 responses and can also modulate T regulatory Lymphocytes (Treg). For example, aluminium salts (Alum), widely used in human vaccination, induce predominantly a Th2 immune response. On the contrary, combinations with complete Freund's adjuvant (CFA), cationic peptides such as 1031 or polyarginine (Schellack et al, Vaccine 24 (2006) 5461-5472; Mitsui et al, J Invest Dermatol. 2006; 126(8):1804-12), heat-shock protein (Moroi et al, Proc Natl Acad Sci USA. 2000; 97(7):3485-90), TLR9 agonists, incorporation of the antigens into ISCOMS (immunostimulating complex) or liposomes (Taneichi et al, J Immunol 2006; 177:2324-2330) can bias the immune response toward a Th1 profile.

Despites all the progress made, several limitations are still faced by modern vaccines. Subunit antigens are often poorly immunogenic. The dose of antigen required to trigger the immunity (usually within the range of 10 to 100 µg) might be a limiting factor, especially when antigen is difficult to manufacture, or when demand exceeds production capacity. Moreover, induction of CD8+ responses remains a difficult challenge because extracellular molecules are usually presented by MHC class II and not by MHC class I. Finally, vaccine formulations, such as emulsion, liposomes, fusion molecules can be either unstable or difficult to synthesize, making the cost of manufacturing sometimes prohibitive. The ideal adjuvant should thus be potent to trigger or boost an Ag-specific immune response (both humoral and cellular responses), easy to manufacture, non toxic, and stable.

Catechols (also known as pyrocatechol or o-hydroxyphenols or 1,2-dihydroxybenzen) play a major role in life and are involved in various biological processes such as neurotransmission, melanogenesis, marine biology, melanization in insects (Eleftherianos et al, J Innate Immun 2011; 3:28-33; Viljakainen, Brief Funct Genomics. 2015; 14(6): 407-12), or sclerotization of arthropod cuticle (Andersen, Insect Biochem Mol Biol. 2010; 40(3):166-78).

Catecholamines are neurotransmettors that are synthesized from L-tyrosine by a series of enzymatic pathways. First, tyrosine hydroxylase removes a hydroxyl group to produce L-DOPA (3,4-dihydroxyphenylalanine). L-DOPA is decarboxylated to form dopamine by L-aromatic amino-acid decarboxylase (LADCC); which is then catabolized to noradrenaline and adrenaline by hydroxylases Dopamine betahydroxylase (DB) and Phenylethanolamine-N-methyl-transferase (PNMT) (Eisenhofer 2003, FASEB J. 2003; 17(10): 1248-55).

Besides their role as precursors of catecholamines, catechols have the ability to undergo oxidation, generating chemical compounds with strong adhesive properties on substrate/other molecules, either by covalent or non-covalent bounds. Such oxidative process plays a major role in various biological processes such as melanogenesis, marine biology, melanization in insects, or sclerotization of arthropod cuticle.

Melanin synthesis plays a major role in animals to protect them against the harmful and mutagenic ultraviolet light rays. In insects, activation of phenoloxidase (PO) also leads to the formation of melanin around intruding microorganisms, a process named melanization, that allows encapsulation of foreign particles (Eleftherianos, 2011, op. cit.; Viljakainen 2015, op. cit.). In general, melanins are macromolecules formed by oxidative polymerization of phenolic or indolic compounds via a series of enzymatic and non-enzymatic reactions (Slominski et al, Physiol Rev. 2004; 84(4):1155-228). L-Dopa is a well-known precursor of melanin (FIG. 1). However, melanins are heterogeneous compounds, and 4 types of melanin have been described: (1) Eumelanins produced by serial oxidations of L-Dopa and leading mainly to copolymers of Dihydroxyindole carboxylic acid (DHICA) and 5,6-dihydroxyindole (DHI); (2) Pheomelanins in which L-Dopa undergoes cysteinylation, by conjugation with glutathione or cysteine, leading to polymers containing benzothiazine and benzothiazole; (3) Neuromelanin (NM) which is produced in specific populations of catecholaminergic neurons in the brain; (4) and, mainly found in many fungi and plants, allomelanins or catechol melanins resulting from oxidation or polymerization of various compounds such as di- or tetra-hydroxynaphthalene, homogentisic acid, y-glutaminyl-4-hydroxybenzene, catechols, 6-hydroxy-Dopa, dihydrocaffeic acid, caffeic acid, catechins, leucoanthocyanidins, 3-amino-tyrosine, 4-hydroxyphenylacetic acid or others cathecols (U.S. Pat. No. 6,576,268; Langfelder et al, Fungal Genet Biol. 2003; 38(2):143-58, Sugumaran et al, FEBS Lett. 1989; 255(2):345-9).

Melanin is thus a broad and generic term for designating a group of natural pigments found in most organisms (arachnids are one of the few groups in which it has not been detected), usually produced by the oxidation of the amino acid tyrosine, followed by polymerization.

Wikipedia (https://en.wikipedia.org/wiki/Melanin) defines melanin as natural pigments (i.e. a colored material), produced by the oxidation of the amino acid tyrosine, followed by polymerization. This oxidation, which is a critical step, is generally mediated by the enzyme tyrosinase, which will convert tyrosine to DOPA.

News Medical Life Science (http://www.news-medical.net/health/What-is-Melanin.aspx) defines melanin as a complex polymer derived from the amino acid tyrosine, by various steps including catalysis of the L-3,4-dihydroxyphenylalanine by tyrosinase.

Melanin is also defined and claimed in EP 313380 as "a major class of broad-spectrum ultraviolet-absorbing organic polymers found naturally in various vegetables (mushrooms), animal species (squid, octopus, etc.) and, very importantly, in the human epidermis. They are formed in the epidermis by the enzymatic conversion of L-tyrosine into L-3,4-dihydroxyphenylalanine, commonly referred to as L-dopa. The L-dopa is further converted to a melanin by a biologic pathway which is well described in the literature."

From http://www.skinwhiteningscience.com/melanin_synthesis_pathways.html, one can see that melanin is obtained through a complex process (as reminded in FIG. 1) that combines both the oxidation of melanin precursors and their subsequent polymerization. This combined process is thus different from the mere polymerization of melanin precursors such as a polytyrosine for instance.

Melanin can be synthetically produced and is sold as such, for instance by Sigma Aldrich, as prepared oxidation of tyrosine with hydrogen peroxide. (http://www.sigmaaldrich.com/catalog/product/sigma/m8631?lang=fr&region=FR From the above, it results that melanin represents a polymeric pigment known and recognized in the art which cannot be confused with a mere polypeptide of amino-acids that are melanin precursors. In particular, a polytyrosyl, obtained without oxidative polymerization would not be considered as a melanin molecule by a person skilled in the art.

Melanin synthesis involves several intermediary compounds, several enzymes and can be modified by pH, presence of cationic metals, temperature.

As intermediary compounds, one could cite: L-phenylalanine, L-tyrosine, L-dopa, dopaquinone, cyclodopa, dopachrome, quinone methide, benzothiazole, benzothiazine, dihydroesculetin, Dihydroxyindole carboxylic acid (DHICA), 5,6-dihydroxyindole (DHI), dopamine-o-quinone, Dopamine Leukoopaminochrome, dopaminoichrome, norepinephrine, noradenochrome, epinephrine, adenochrome, 3-amino-tyrosine, and others.

As enzymes involved in the synthesis, one could cite: Phenylalanine hydroxylase, tyrosinase (EC 1.14.18.1 and EC 1.10.3.1), mushroom tyrosinase, tyrosine hydroxylases, peroxidase, Phenol-oxidase, Dopachrome tautomerase (E.C. 5.3.2.3, DCT/Trp2); DHICA oxidase (Trp1) DHI oxidase.

Synthesis of melanins and the predominant melanin type are strongly influenced by the presence of cysteine residues (leading to pheomelanin as mentioned above), pH (alcaline pH promoting auto-osxidation of catechol), metal ions (such as $CU^{2+}$, $Ni^{2+}$, $Fe^{3+}$, $Fe^{2+}$, $Co^{2+}$ . . . ) (Palumbo et al, Biochim Biophys Acta. 1987; 13; 925(2):203-9; Palumbo et al, Biochim Biophys Acta. 1991; 1115(1):1-5; WO 1995009629 A1), and the enzymes added in the incubations. For example, Pawelek (1993, 1995) described a method to produce soluble synthetic melanin by combining dopachrome and an appropriate enzyme, or by incubating 5,6-dihydroxyindole-2-carboxylic acid alone or with 5,6-dihydroxyindole, or with 3-amino-tyrosine (U.S. Pat. Nos. 5,225,435; 5,384,116).

In marine biology, Mussel Adhesive Proteins (MAPs) have the ability to form strong adhesive bond with various substrates in wet environment. These adhesive proteins contain an unusually high proportion of L-Dopa, which after oxidative polymerization (thus leading to melanin-like compounds) is largely responsible for their adhesive strengths (Lee et al, Biomacromolecules 2002, 3, 1038-1047; Wang et al, Biomaterials 28 (2007) 3456-3468). Several primary catecholamines, such as Norepinephrine, Dopamine, or Dopa-containing polymers can undergo similar oxidative polymerization that can build up adhesive films on the surfaces of solid materials (Lee, op. cit.; Wang, op. cit.; Guvendiren et al, Adhes. 2009; 85(9): 631-645; Wei et al, Colloids Surf B Biointerfaces. 2013; 110:22-8).

In arthropods, cuticular sclerotization is a process closely related to melanization, by which cuticles are stabilized by incorporation of phenolic compounds. Sclerotization mainly involves 3 catechols (N-acetyldopamine (NADA), dehydro- NADA and N-b-alanyldopamine (NBAD)) that are first oxidized to ortho-quinones by tyrosinase or laccase. The corresponding ortho-quinones can be rearranged to para-quinone methides and further oxidized to unsaturated quinoid derivatives and dehydro-benzodioxine derivatives. The ortho-quinones and para-quinone methides are highly reactive compounds and can form adducts by reaction with nucleophilic compounds (such as cysteine, histidine, methionine, lysine, alanine, tyrosine) to give acyldopamines substituted in the 6-position of the aromatic ring (mainly for ortho-quinone) or substituted in the beta-position of the side chain (for para-quinone methides) (Andersen 2010, op. cit.).

Some authors raised the hypothesis that melanogenesis can also play a role in innate immunity (Mackintosh et al, J. theor. Biol. (2001) 211, 101-113). This hypothesis is mainly supported by the ability of insects to activate phenoloxidase (PO), that leads to the formation of melanin around intruding microorganisms, a process named melanization, that allows encapsulation of foreign particles (Eleftherianos et al, J Innate Immun 2011; 3:28-33; Viljakainen 2015, op. cit.).

The situation might be the opposite in mammals as it is well recognized that melanin synthesis by *Cryptococcus neoformans* (but also some species of pathogenic bacteria and helminthes) actually increases its virulence by protecting the fungus against phagocytosis and phagocytic killing by the host (Casadevall et al, 2000, Curr Opin Microbiol. 2000 August; 3(4):354-8). Synthetic melanin suppresses cytokine production in macrophages stimulated with lipopolysaccharide (Mohagheghpour et al, Cell Immunol. 2000; 199(1):25-36), although fungal melanin can activate the alternative complement pathway (Rosas et al, Clin Diagn Lab Immunol. 2002; 9(1):144-8). C57BL/6 mice that differed only in the gene encoding tyrosinase, a key enzyme in the synthesis of melanin, showed no difference in the clinical course of malaria infection (Waisberg et al, PLoS One. 2012; 7(1):e29493).

There is no mention in the literature that L-Dopa or melanin can promote an adaptive immune response such as antibodies or cytotoxic T-Lymphocytes. In particular, immunological studies have revealed that Dopa-containing polymers are poor antigens (Lee et al, Adv Mater. 2009; 21(4): 431-434; Wei, 2013, op. cit.; Ball et al, J Colloid Interface Sci. 2012 15; 386(1):366-72).

In a murine model of anterior uveitis, immunization against a bovine, insoluble retinal pigment epithelium (RPE) fraction has been described (Boral et al, Invest Ophthalmol Vis Sci. 1995; 36(6):1056-66). Interestingly, the pathogenic antigen, still unknown, is bound to large spindle-shaped mature melanin particles (approximately 2-3 µm long) (Broekhuyse et al, Exp Eye Res. 1992; 55(3):401-11). However, the melanin appears as a companion during the purification process, as the antigen remains pathogenic even after antigen solubilisation by V8 protease (table 5, Bora 1995), making the role of melanin in the physiopathology of the disease unlikely. Other examples of such association have not been described in the literature.

Direct modulation of the immune system by the neurotransmitter dopamine through autocrine/paracrine manner has been suggested. Dopamine shows conflicting effects on the immune system. Dopamine can potentiate the production of Th2 cytokines by human naïve CD4 T-cells, of Th1 cytokines by activated CD4 T-cells; or of Th17 cytokines (IL-23) by DCs. Dopamine can inhibit the suppressive activity of regulatory T-cells (T-reg), favor T-cell migration, but can also inhibit human T-cell proliferation (Sarkar et al, Brain Behav Immun. 2010; 24(4): 525-528; Pacheco et al, Front Immunol. 2014; 5:117). Altogether, the effects of Dopamine on the immune system are complex and not straightforward. These effects do not directly trigger an antigen-specific immune response, are mediated by DARs and do not require a close vicinity between the antigen and dopamine.

It has also been reported that 5,6-dihydroxyindole-2-carboxylic acid (DHICA)-melanin plays a role in the maintenance of immune hyporesponsiveness to melanosomal proteins via DHICA-mediated antioxidation (Liu et al, Free Radic Biol Med. 2011 May 1; 50(9):1177-85).

Other authors have reported some anti-inflammatory and immunomodulating properties of grape melanin. Inhibitory effects on paw edema and adjuvant induced disease. (Avramidis et al; Arzneimittelforschung. 1998 July; 48(7):764-71). In particular, the authors reported an inhibitory effect of melanin on carrageenin-induced edema, as well as on edemas produced by other phlogistics, and that grape melanin showed potent inhibitory effect on adjuvant induced disease (AID) in rat. The authors indicated that the observed effect may be due to the possible inhibition of the cellular immune responses mediated by lymphocytes subpopulation Th1 (T4+ or T8+) by melanin.

In summary, the role of melanin or its precursors with regards to immunity remains elusive. Arnon et al (1960—Biochem. J., 75: 103-109) disclose among others, antigen protein, i.e. gelatin, egg albumin or edestin, bound to polytyrosyl, which is not a melanin I.

Sela et al (Biochem. J., vol. 75, 1 Jan. 1960, pages 91-102) disclose an operating process for obtaining polypeptidyl gelatin. There is no oxidative polymerization and the obtained product does not comprise melanin and cannot be considered as a melanin.

Akagi et al (In: "Bioactive Surfaces", 1 Jan. 2011, Springer Berlin Heidelberg, Berlin, Heidelberg, Adv Polym Sci, vol. 247, pages 31-64) disclose Biodegradable Nanoparticles as Vaccine Adjuvants and Delivery Systems.

Polyaminoacid nanoparticles are prepared with tyrosin, but this document does not disclose nor mention melanin or that the polymerization would give melanin as the final product.

US 2004/057958 discloses an immunogenic carrier which can be a polyamino acid polymer. This document never mentions or suggests to use melanin as an immunogen.

Fujita et al (Chemistry Central Journal, Biomed Central Ltd, vol. 5, no. 1, 23 Aug. 2011, page 48) reviews the status of multiple antigen-presenting peptide vaccine systems, using nanoparticles. This document does not mention nor suggest to prepare complexes of melanin and antigens for increasing immunogenicity of the antigen.

Cui et al (Biomacromolecules, vol. 13, no. 8, 13 Aug. 2012, pages 2225-2228) describes use of polydopamine films (which are different from melanin) on capsule to perform intracellular drug delivery. The particles are not used to obtain an immunogenic composition.

Cui et al (NANO, vol. 10, no. 05, 1 Jul. 2015, pages 1530003-1 to 1530003-23) further disclose poly-dopamine capsules. The particles are not used to obtain an immunogenic composition.

Lee et al (Advanced Materials, vol. 21, no. 4, 26 Jan. 2009, pages 431-434) disclose that polydopamine films can be bioconjugated to various substrates, but do not indicate that these films display immunogenic properties.

Park et al (ACS Nano, vol. 8, no. 4, 22 Apr. 2014, pages 3347-3356) disclose polydopamine nanoparticles used for carrying drugs. This document does not mention or suggest melanin-antigen complexes as immunogenic compositions.

US 2012/237605 discloses nanoparticules with a polydopamine-based surface, but does not suggest or disclose the use thereof as immunogenic compositions.

Liu et al (Small. 2016 Apr. 6; 12(13):1744-57) disclose pathogen-mimicking polymeric nanoparticles based on dopamine polymerization as vaccines adjuvants induce robust humoral and cellular immune responses. Antigen is added after formation of the melanin.

The invention is based on the fact that melanin can be used as a potent adjuvant for inducing immunity against an antigen, when administered conjointly with this antigen. It is preferred when the melanin and the antigen are complexed, in particular when the antigen is trapped within the melanin.

Definitions

In the context of the present invention, the following terms have the following meanings:

Melanin

A "melanin" is a pigment being a macromolecule obtained from the oxidative polymerization of precursors related to indole or catechol. FIG. 1 describes the synthesis of one type of melanin (eumelanin). A melanin according to the present invention may be a "natural" melanin that could be found in nature, such as the eumelanin obtained from the polymerization of the precursors as depicted in FIG. 1, a MAPs-like polymer (containing a high proportion of a melanin precursor), or a melanin-like molecule obtained from the polymerization of precursor derivatives such as the ones described below.

There are multiple melanins which are produced by the oxidation of the amino acid tyrosine, followed by polymerization: eumelanin, pheomelanin, and neuromelanin and plant melanins.

A preferred melanin, in the context of the present application, is eumelanin. However, the composition described below and used in the composition of the invention may also use other types of melanins such as pheomelanins, neuromelanins, plant melanins, MAPs-like polymers (obtained from oxidation of polymers containing a high proportion of a melanin precursor such as L-Dopa) which can be considered as melanin-like molecules, as well as non-natural melanins obtained through polymerization of derivatives of melanin precursors.

The first step of the biosynthetic pathway for both eumelanins and pheomelanins is catalysed by tyrosinase that promotes the oxidation of its substrates (FIG. 1):

Tyrosine→DOPA→dopaquinone

Dopaquinone can combine with cysteine by two pathways to benzothiazines and pheomelanins Dopaquinone+cysteine→5-S-cysteinyldopa→benzothiazine intermediate→pheomelanin Dopaquinone+cysteine→2-S-cysteinyldopa→benzothiazine intermediate→pheomelanin Also, dopaquinone can be converted to leucodopachrome and follow two more pathways to the eumelanins Dopaquinone→leucodopachrome→dopachrome→5,6-dihydroxyindole-2-carboxylic acid (DHICA)→quinone→eumelanin Dopaquinone→leucodopachrome→dopachrome→5,6-dihydroxyindole (DHI)→quinone→eumelanin Melanin Precursor A "melanin precursor" is a molecule that is used or synthetized during the synthesis of a melanin. In particular, one can cite: L-phenylalanine, L-tyrosine, L-dopa, dopaquinone, cyclodopa, dopachrome, Dihydroxyindole carboxylic acid or 5,6-dihydroxyindole-2carboxylic acid (DHICA), indol 5,6 quinone, 5,6-dihydroxyindole (DHI), dopamine-o-quinone, Dopamine leukodopaminochrome, leukodopachrome (cyclodopa), dopaminochrome, norepinephrine, noradequinone, noradenochrome, epinephrine, epinephrine-o-quinone, adenochrome, 3-amino-tyrosine, 6-hydroxy-Dopa, dihydrocaffeic acid, caffeic acid and others.

L-tyrosine is a preferred precursor, and would require oxidative polymerization. L-dopa is a preferred precursor.
D-dopa is a preferred precursor.
6-hydroxy-Dopa is a preferred precursor.
DHICA is a preferred precursor.
DHI is a preferred precursor.
A mixture of DHICA and DHI is a preferred precursor.
Dopamine is a preferred precursor.

The term "melanin precursor" further includes derivatives of such precursors and/or polymers containing a high proportion of such precursors (such as in Mussel Adhesives Proteins).

One can choose, in particular:
a chemical compound containing a cathecol moiety

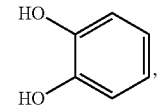, or its relative ortho-benzoquinone moiety

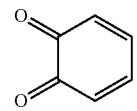

such as: L-Dopa, D-Dopa, Dopamine, norepinephrine (noradrenaline), epinephrine (adrenaline), 6-hydroxydopa, catechin, dihydrocaffeic acid, caffeic acid, (3,4-dihydroxyphenylacetic acid) DOPAC; 3,4-Dihydroxymandelic acid, acyldopamines, N-acetyldopamine, dehydro-N-acetyldopamine and N-b-alanyldopamine, dopaquinone, dopamine-o-quinone, norepinephrine-o-quinone, epinephrine-o-quinone.

A particularly preferred material is L-DOPA (L-3,4-dihydroxyphenylalanine), D-DOPA (D-3,4-dihydroxyphenylalanine), 6-hydroxydopa, or substituted derivatives thereof

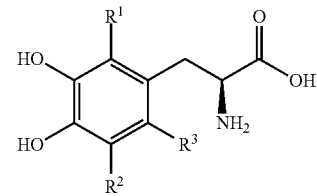

In which R1, R2 and R3 are independently hydrogen —OH, or C1 to C6 alkyl groups.

A precursor of cathecol moiety, such as: phenylalanine, Tyrosine, tryptamine
a chemical compound containing a indole-5,6-diol moiety

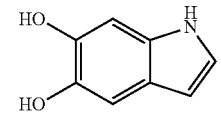 [SMILES: Oc1cc2cc[nH]c2cc1O]

or its relative Indoline-5,6-diol moiety

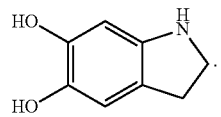

such as: Dopachrome, Dopaminochrome, noradrenochrome, adrenochrome, DHICA, Indol 5,6 quinone, LeukoDopachrome (cycloDopa), Leucodopaminechrome; leuconoradrenochrome, 5,6-dihydroxyindole-2-carboxylique (DH ICA), 5,6-dihydroxyindole (DHI)

A particularly preferred material is DHICA.

a chemical compound containing a indole moiety of the formula

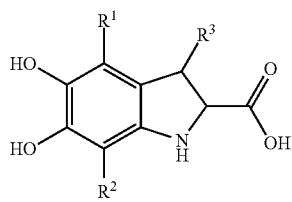

in which R1, R2 and R3 may be the same or different and are independently hydrogen, —OH or C1 to C6 alkyl groups.

Other derivatives are known in the art. One can cite, as an illustration, 6-dihydroxyindole (DHI) Derivatives Examples of DHI derivatives that can be used in the process of the invention are the ones described in WO 98051269, in particular the a dihydroxyindole being represented by the formula (I):

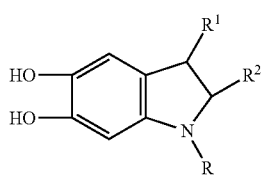

where

R is chosen in the group consisting of an hydrogen, an alkyl group with 1 to 6 carbon atoms, an hydroxyalkyl group with 1 to 6 carbon atoms, an aminoalkyl group with 1 to 6 carbon atoms, an aryl, and a substituted aryl containing up to three reaction inert substituents;

R1 and R2, may be the same or different, and are chosen in the group consisting of hydrogen, alkyl containing from one to six carbon atoms, or, when R2 is H, R1 may represent COOR3, wherein R3 is H or an alkyl having from one to six carbons.

Alternatively, compounds as described in EP 441689 can also be used, such as the ones of formula (II)

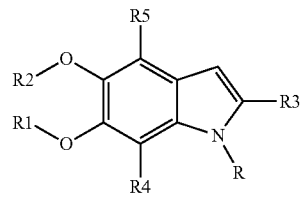

wherein:

R represents a hydrogen atom, alkyl, alkoxy, hydroxyalkyl, aminoalkyl, SiR6R7R8 wherein R6, R7, R8 denote alkyl, wherein alkyl comprises it from 1 to 8 carbon atoms or an unsubstituted or substituted aryl radical OH, $NH_2$, alkyl, alkoxy or $NO_2$;

R1 and R2, identical or different, represent $C_1$-$C_3$ alkyl or together form a methylene or ethylene group optionally substituted by one or more $C_1$-$C_3$ alkyl, R3 is hydrogen or COOH, R4 and R5, identical or different, represent an hydrogen atom, an hydroxyl group, a methyl or a $C_2$-$C_6$ alkyl.

One can cite, in particular, 5,6-dimethoxyindole, 5,6-methylenedioxyindole and 1-methyl-5,6-dimethoxyindole.

DOPA Derivatives

One can use DOPA derivatives, as disclosed in EP 58040, in particular, chosen from:

(a) mono and/or di-substituted ester and formate derivatives of DOPA having the formula (III):

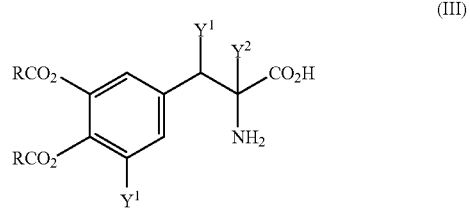

where R is —H, a branched or unbranched, alkyl or alkenyl group having from 1 to 20 (preferably 1 to 6) carbon atoms, or an amino acid or peptide fragment, $Y^1$ is —H or —OH, or —CH3 or any other C2 to C6 alkyl group, and $Y^2$ is —H or —$CH_3$;

(b) mono and/or di-substituted carbonate derivatives of DOPA having the formula:

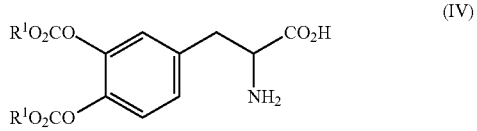

where $R^1$ is a branched or unbranched, alkyl or alkenyl group having from 1 to 20 carbon atoms;

(c) mono and/or di-substituted urethane derivatives of DOPA having the formula (V):

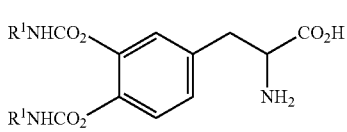
(V)

wherein R1 is an oxygen or a C1-C3 alkyl group (d) mono and/or di-substituted ether derivatives of DOPA having the structure (VI):

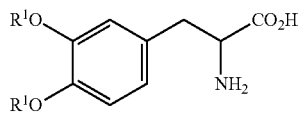
(VI)

wherein R1 is an oxygen or a C1-C3 alkyl group (e) mono and/or di-substituted phosphate and/or sulphate derivatives of DOPA having the structure (VII):

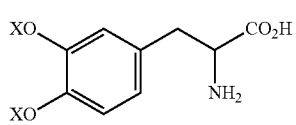
(VII)

where one X is —PO☐H? or —SO☐H and the other X is —H, —PO$_3$H$_2$ or —SO$_3$H;

(f) acetal and ketal derivatives of DOPA having the structure (VIII):

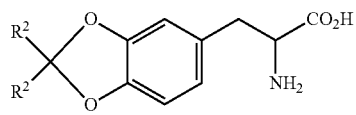
(VII)

where R$^2$ is chosen from —H, alkyl and phenyl;

(g) cyclic carbonate derivatives of DOPA having the structure (IX):

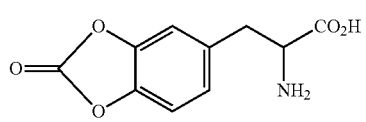
(IX)

(h) amino substituted derivatives of DOPA having the structure (X):

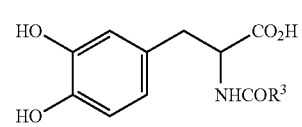
(X)

where R$^3$=R$^1$ as disclosed above, or an amino acid residue;

(i) carboxylate substituted derivatives of DOPA having the structure (XI):

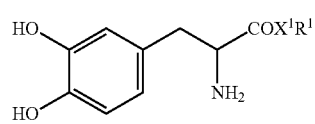
(XI)

where X$^1$ is an NH amide (especially an amino acid or peptide) linkage;

(j) linked amino and carboxylate substituted derivatives of DOPA having the structure (XII):

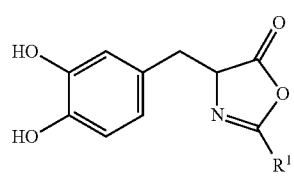
(XII)

where R$^1$ is as described above (k) structural analogues of DOPA having the structure (XIII):

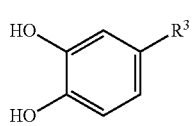
(XIII)

where R$^3$ is chosen from:

(i)

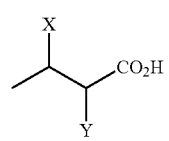

where X$^2$ is the same or different and is chosen from —H, —OH, —NH$_2$ or —SH

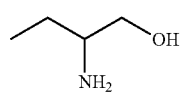
(ii)

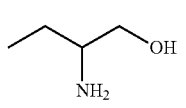
(iii)

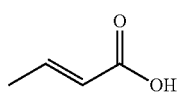
(iv)

(l) structural analogues of DOPA having the structure (XIV):

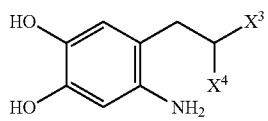  (XIV)

where
$X^3$ is —OH or $OR^1$
$X^4$ is =O or $OR^1$ (m) C-homologues of DOPA having the structure (XV):

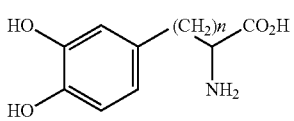  (XV)

where n is an integer of from 1 to 3;

(n) short chain and hetero atom analogues of DOPA having the structure (XVI):

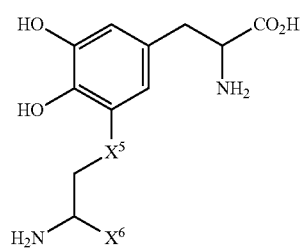  (XVI)

where
$X^5$ is S, O or NH and
$X^6$ is H or COOH; and (o) a glutathione derivative having the structure (XVII):

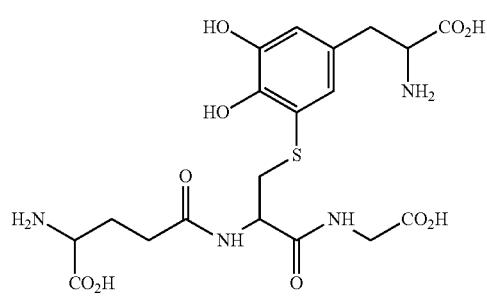  (XVII)

The substituted DOPA may also be chosen from:
3,4-dihydroxyphenylserine, having the structure:

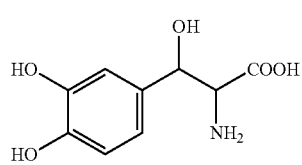 [SMILES: NC(C(=O)O)C(O)c1ccc(O)c(O)c1]

2,4,5,-trihydroxyphenylalanine, having the structure:

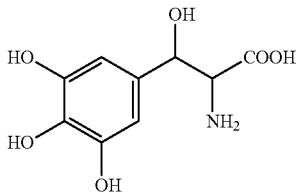 [SMILES: NC(C(=O)O)C(O)c1cc(O)c(O)c(O)c1]

6 hydroxy Dopa, having the structure

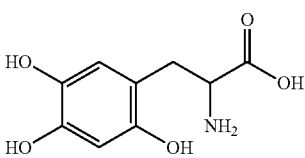 [SMILES: NC(Cc1cc(O)c(O)cc1O)C(=O)O]

2-methyl-3-(3,4-dihydroxyphenylalanine), having the structure:

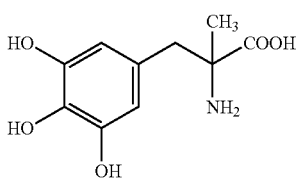 [SMILES: CC(N)(Cc1cc(O)c(O)c(O)c1)C(=O)O]

Another possibility is methoxytyrosine having the structure:

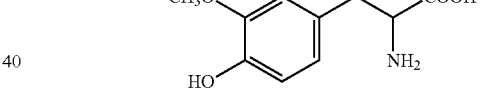

and its isomer 3-hydroxy-4-methoxyphenyl alanine of structure:

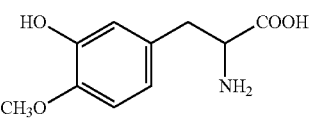

Such as described in EP 580409.

DHICA Derivatives

As an illustration of such derivatives, one can use

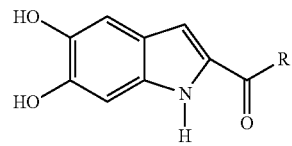

where R is chosen in the group consisting consisting of an hydrogen, an alkyl group with 1 to 6 carbon atoms, an hydroxyalkyl group with 1 to 6 carbon atoms, an aminoalkyl group with 1 to 6 carbon atoms, an aryl, and a substituted aryl containing up to three reaction inert substituents, COOH, NH$_2$.

Other melanin precursors or derivatives thereof are described in the art, such as the products described in WO 93/021898.

The term "melanin precursor" also encompasses polymeric molecules containing a high proportion of melanin precursors as disclosed above that are able to undergo polymeric oxidation. As an example, one could cite poly-Dopa peptides, poly-Tyrosine peptides, or more generally any polymers containing a high proportion of melanin precursors (such as the precursors of Mussel Adhesives Proteins).

Oxydizing Agent

An "oxidizing agent" or "oxidizing molecule" is a compound that is able to provide oxygen to a solution containing melanin precursors and promote polymerization thereof and formation of a melanin macromolecule.

Oxidizing agents that can achieve this goal comprise oxygen, hydrogen peroxide, ammonium persulfate, ferric ions, sodium iodide together with hydrogen peroxide, and treatment with a salt of a transition metal cation such as copper sulfate as a catalyst for air oxidation.

It is thus preferred when the oxidizing agent is chosen in the group consisting of oxygen, hydrogen peroxide, ammonium persulfate, and ferric ions.

Immunogenic or Immunostimulatory Composition

An "immunogenic or immunostimulatory composition" is a composition that is able to generate an immune response in an animal when administered to said animal. Preferably, said animal is a mammal, but is can also be a bird (such as a chicken, a duck, a goose, a turkey, a quail), in particular when the composition is used in avian livestock. The animal may also be a fish, as the immunogenic composition may be used in fish farming.

However, an immunogenic composition according to the invention is preferably used in mammals. Such mammals are preferably human beings, but can also be other mammals, when the composition is used in the veterinary field, in particular for inducing immunity in livestocks such as cattle (cows), sheeps, goats or horses, but also for pets such as dogs or cats.

The immunogenic composition is thus a composition that contains an antigen and that is able to generate a immune response against such antigen. The generated immune response can be a cellular (T-cell mediated) or a humoral (B-cell mediated, production of antibodies) immune response. The immunogenic composition may also induce both a cellular and a humoral immune response. The cellular immune response can be a CD8 T lymphocytes mediated response (ie cytotoxic response), or a CD4 T lymphocytes mediated response (helper response). It can also combine a cytotoxic and helper cellular immune response. The helper response may involve Th1, Th2 or Th17 lymphocytes (such lymphocytes being able to elicit different cytolkine responses, as is known in the art).

The immunogenic composition may allow a better presentation of the antigen present therein, through MHC1 or MHC2 pathways.

Adjuvant

An "adjuvant" is a substance that has the capacity to modify or enhance the immune response to an antigen. In other words, the immune response against the antigen may be higher or different in the presence of the adjuvant than when the adjuvant is not present (that includes when the response is modified, for example when the subset of T cells that are activated in the presence of the adjuvant is different from the subset activated in the absence of the adjuvant). Adjuvants are known in the art and have been widely used in the vaccine field.

One can cite alum, emulsions (either oil-in-water or water-in-oil, such as Freund's Incomplete Adjuvant (IFA) and MF59®), PRR (Pattern recognition receptors) Ligands, TLR3 (Toll-Like Receptor 3) and RLR (RIG-I Like Receptors) ligands such as double-stranded RNA (dsRNA), or synthetic analogs of dsRNA, such as poly(I:C), TLR4 ligands such as bacterial lipopolysaccharides (LPS), MPLA (monophosphoryl lipid A), in particular formulated with alum, TLR5 ligands such as bacterial flagellin, TLR7/8 ligands such as imidazoquinolines (i.e. imiquimod, gardiquimod and R848), TLR9 ligands such as oligodeoxynucleotides containing specific CpG motifs (CpG ODNs) or NOD2 (Nucleotide-binding oligomerization domain-containing protein 2) ligands. The term ligand above describes preferably an agonist of the receptor, i.e. a substance that binds to the receptor and activates the receptor, in particular for TLR3 and TLR9 receptors.

Antigen

In the context of the invention, an "antigen" is an antigen is a molecule or a combination of molecules against which it is desired to elicit a immune response in order for the immune system of a living animal to recognize it. Such antigen may be foreign to the body of the host to which the immune response is sought. In this case, the antigen may be a protein expressed by a bacteria or a virus. The antigen may also be a self-antigen, ie a protein that is expressed by cells of the host, such as tumor antigens.

Antigens can consist of whole organisms (viruses or bacteria, fungi, protozoa or even cancer cells), killed or not, cells (irradiated or not, genetically modified or not), or subfractions of these organisms/cells like cell extracts or cell lysates. Antigens can also consist of single molecules like proteins, peptides, polysaccharides, lipids, glycolipids, glycopeptides or mixture thereof. Antigens may also be one of the above-cited molecules that has been modified through a chemical modification or stabilisation. In particular, the net charge of the antigen can be modified using adequate substitution of amino acids or chemical modifications of the antigen.

An antigen may be a full protein, or any part of a protein, such as an epitope of the protein. The antigen, in the context of the present invention may also consist in a synthetic protein or molecule that contains multiple epitopes that are linked together.

In particular, the antigen may be a protein containing multiple epitopes of the same antigen, these epitopes being specific of a MHC haplotype. In this case, one can use a unique immunostimulatory molecule as described herein to obtain a immune response in in different genetic (MHC) context.

In another embodiment, the antigen may be a protein containing multiple epitopes obtained from various antigens of the same pathogen (the term pathogen preferably indicate a foreign pathogenic agent such as a bacteria, a virus, a parasite or a fungus, but may also extend to tumour cells). In this case, one can use the immunostimulatory molecule to obtain a strong immune response against this pathogen.

The antigen that can be used with the melanin macromolecule in the disclosed composition is any antigen against which a immune response is searched.

This antigen can be a full protein as found in nature, or only part of a protein found in nature.

The antigen as intended in the immunogenic composition as herein described, can also be a mixture of antigens.

The antigen may be a protein, a peptide, a polysaccharide, or a lipid. The antigen may be part (coats, capsules, cell walls, flagella, fimbrae, and toxins) of a bacteria, a virus, or another microorganisms. The antigen may a a more complex molecule such as a lipid combined with a protein and/or a polysaccharide.

Epitopes

In a particular embodiment, the antigen as used in the immunogenic composition comprises one or several MHC epitopes.

In a particular embodiment, the antigen as used in the immunogenic composition consists in a MHC epitope.

In another embodiment, the antigen as used in the immunogenic composition consists in a MHC epitope which is flanked, at its N and/or C terminus by a few amino-acids (between 1 and 10, preferably between 1 and 6 amino-acids at one, or both C and N terminal ends).

A MHC epitope (or T cell epitope) is presented on the surface of an antigen-presenting cell, where they are bound to MHC molecules. T cell epitopes presented by MHC class I molecules are typically peptides between 8 and 11 amino acids in length, whereas MHC class II molecules present longer peptides, 13-17 amino acids in length (https://en.wikipedia.org/wiki/Epitope#T_cell_epitopes).

The MHC epitope may be synthetized in vitro (with or without addition of amino acids at its C and/or N terminal extremities). MHC bound peptides may be extracted from live cells, in particular tumor cells, by any method known in the art such as acid treatment in particular with hydrochloric acid.

In another embodiment, the antigen comprises one or several B cell epitopes, i.e. part of a protein that is recognized by an antibody, preferably linear epitopes, formed by a continuous sequence of amino acids from the antigen.

In a particular embodiment, the antigen as used in the immunogenic composition consists in a B cell epitope.

In another embodiment, the antigen as used in the immunogenic composition consists in a B cell epitope which is flanked, at its N and/or C terminus by a few amino-acids (between 1 and 10, preferably between 1 and 6 amino-acids at one, or both C and N terminal ends).

Different methods in the literature, relating to epitope mapping, make it possible to identify T cell or B cell epitopes from a given antigen.

However, the composition as disclosed herein makes it possible to only use the epitopes that are already known from known antigens (which are thus well characterized), rather than full proteins. The fact to use only epitopes (i.e. small antigenic parts) to elicit a immune response is particularly interesting to limit any adverse effects that could be associated with the use of large size proteins.

Other Synthetic Antigens

In particular, the antigen may be a synthetic molecule comprising multiple epitopes, separated by stretches of amino acids or any other acceptable linkers such as polyether compounds or other linkers used in dendrimer constructs (Tam, Proc Natl Acad Sci USA. 1988, 85(15): 5409-13; Seelbach et al, Acta Biomater. 2014 10(10):4340-50; Sadler and Tam, Reviews in Molecular Biotechnology 90, 3-4, pp 195-229; Bolhassani et al, Mol Cancer. 2011 Jan. 7; 10:3).

The multiple epitopes may be epitopes specific for different HLA genotypes (in order to generate a single immunogenic or immunostimulatory composition that able to elicit a immune response against a given antigen or pathogen in a broad population of patients.

In another embodiment, the epitopes may originate from the same or multiple antigens of the same pathogenic agent, in order to elicit a strong immune response against said pathogenic having the multiple epitopes.

In another embodiment, the epitopes may originate from different pathogenic agents, in order to elicit a immune response against these various agents at one time, by using the immunogenic composition.

The antigen may contain universal T helper epitopes such as pan-DR epitope (PADRE) and $Pol_{711}$ epitopes. The literature widely discloses other universal T helper epitopes.

Source of the Antigens

Antigens that can be used in the present invention can be chosen in particular among:

Exogenous antigens (antigens that have entered the body from the outside, for example by inhalation, ingestion or injection; these antigens are generally presented by MHC II molecules).

Endogenous antigens (antigens generated within normal cells as a result of normal cell metabolism, or because of viral or intracellular bacterial infection; these antigens are generally presented by MHC I molecules).

Neoantigens (such as tumor antigens, such as epitopes derived from viral open reading frames in virus-associated tumors, or other tumor antigens presented by MHC I or MHC II molecules on the surface of tumor cells.

Allergens (an antigen capable of stimulating a type-I hypersensitivity reaction in atopic individuals through Immunoglobulin E (IgE) responses).

As examples of tumor antigens, one can cite alphafetoprotein (AFP) found in germ cell tumors and hepatocellular carcinoma, carcinoembryonic antigen (CEA) found in bowel cancers, CA-125 found in ovarian cancer, MUC-1 found in breast cancer, epithelial tumor antigen (ETA) found in breast cancer, tyrosinase or melanoma-associated antigen (MAGE) found in malignant melanoma, abnormal products of ras, p53 found in various tumors, gp100 (Melanocyte protein PMEL, a type I transmembrane glycoprotein enriched in melanosomes), TRP2 (Tyrosinase-Related Protein 2), EPHA2 (receptor tyrosine kinase, frequently overexpressed in a wide array of advanced cancers such as gliomas), survivin (baculoviral inhibitor of apoptosis repeat-containing 5 or BIRC5, expressed in particular in breast and lung cancer), EGFRvIII (epidermal growth factor receptor mutant, expressed in particular in glioblastomas).

As examples of pathogens from which antigens can be used in the immunogenic composition, one can cite any pathogens involved in infectious diseases (virus, bacteria, parasite, mycosis).

For infectious diseases, preferred pathogens are selected from human immune deficiency virus (HIV), hepatitis A and B viruses, hepatitis C virus (HCV), Rous sarcoma virus (RSV), Ebola viruses, Cytomegalovirus, Herpes viruses, Varicella Zoster Virus, Epstein Barr virus (EBV), Influenza virus, Adenoviruses, Rotavirus, Rubeola and rubella viruses, Variola virus, *Staphylococcus, Chlamydiae, Mycobacterium tuberculosis, Streptococcus pneumoniae, Bacillus anthracis, Vibrio cholerae, Helicobacter Pilorii, Salmonella, Plasmodium* sp. (*P. falciparum, P. vivax,* etc.), *Pneumocystis carinii, Giardia duodenalis* (Giardiose), *Schistosoma* (Bilharziose), *Aspergillus, Cryptococcus, Candida albicans, Listeria monocytogenes,* or *Toxoplasma gondii.*

As examples of diseases which can benefit from immunizations with an appropriate antigen one can cite: cancer (benign or malignant tumors); hematological malignancies, allergies, autoimmune diseases, chronic diseases such as atherosclerosis, or Alzheimer disease.

The antigen is thus preferably a bacterial or viral antigen (or a polypeptide or polymer (such as the ones usable in dendrimers) containing one or more epitopes isolated from a bacterial or viral antigen).

In another embodiment, the antigen is a self-antigen (endogenous or neoantigen), in particular a tumor specific antigen (or a polypeptide containing one or more epitopes isolated from such antigens).

In another embodiment, the antigen is an allergen or a polypeptide containing one or more epitopes isolated from such antigen.

Modification of the Antigens

The melanin precursors are generally charged. In particular, the presence of carboxyl groups in such precursor will provide negative charges. Thus DHICA (5,6-dihydroxyindole-2-carboxylic acid) is negatively charged. A contrario, other precursors such as DHI (5,6-dihydroxyindole) are neutral or positively charged.

In order to improve the immunostimulatory property of the composition as disclosed, it is thus preferred when the antigen presents a neutral charge or a charge that is opposite to the charge of the melanin.

Thus, when using Dopa or DHICA as the melanin precursor, one may advantageously use an antigen that is positively charged. In this embodiment though, it is important to note that the whole charge of the antigen doesn't need to be positive, but that the antigen shall present at least a region that is positively charged. This may be obtained by adding tails of positively charged amino acids to the antigen, but other methods (grafting positive moieties to the antigen) may also be used.

When dopamine or DHI are used, the antigen may be neutral or negatively charged.

The purpose of this embodiment is to improve the formation of the melanin-antigen complex in the immunostimulatory composition, by allowing the antigen and the melanin precursor to be close to each other through charge attraction (electrostatic attraction) before oxidative polymerization.

Vaccine

In the context of the invention, a vaccine is a composition that is administered to produce or artificially increase immunity to a particular antigen. It is thus undersood that the terms "immunogenic composition", "immunostimulatory composition" and "vaccine" are synonymous terms.

DETAILED DESCRIPTION OF THE INVENTION

The invention thus relates to an immunostimulatory composition comprising an antigen and a melanin macromolecule. Said composition can be used as a vaccine as will be discussed below.

It is preferred when the antigen and the melanin are complexed to each other. One can easily test that the antigen is complexed with the melanin by performing a thin layer chromatography of the composition and verifying that the antigen is not detectable, or that the majority (more than 50%, more preferably 60%, more preferably 70%, more preferably 80%, or more than 90%) of the antigen initially present in the composition has disappeared. The melanin and the antigen are thus complexed when the two entities are so linked together than they don't migrate separately on thin layer chromatography. In other word, it is not possible to distinguish or separate the two entities in the composition.

Other methods can be used to verify that the antigen and the melanin are complexed, such as HPLC or polyacrylamide gels.

It is to be noted that the percentage of the antigen that is complexed with the melanin depends on the quantity of the melanin precursor present before polymerization thereof. In particular, if the antigen is in large excess as compared to the precursor, there will be a low percentage of the antigen complexed with the melanin macromolecule. In any case, a quantitative analysis method such as HPLC makes it possible to determine that antigen has been complexed within the formed melanin and may be used in the context of the present application.

When the composition has been obtained by polymerization of the antigen and melanin precursor, without being bound to this theory, it is supposed that the antigen has been trapped within the melanin macromolecule thus obtained.

As indicated above, melanin is a macromolecule that is obtained after oxidative polymerization of melanin precursors. It is preferred when the melanin is a soluble melanin in the immunostimulatory composition. A soluble melanin is a melanin that is in the form of particles of small size, ie less than 500 nm, preferably less than 250 nm or less than 200 nm.

It is possible to obtain a soluble melanin composition by filtration of the composition obtained after polymerization with a filter having adapted size of pores.

It is to be noted that, in the presence of oxygen, DHI spontaneously forms a black precipitate, whereas DHICA forms a golden-brown solution (Pawelek, Pigment Cell Res. 1991 March; 4(2):53-62) and that the composition containing soluble melanin-antigen complex is thus preferably obtained from using DHICA, dopachrome (rather unstable though), cyclodopa, dopaquinone or Dopa as the melanin precursor.

Obtaining the Immunogenic Composition

The composition as disclosed above is susceptible to be obtained after polymerization of melanin precursors in the presence of the antigen.

The composition is preferably obtained after polymerization, in particular oxidative polymerization, of melanin precursors in the presence of the antigen.

The antigen may be present in solution with the melanin precursor, or may be bound to the melanin precursor, in particular by a covalent bound. Such embodiment may be obtained by linking a melanin precursor to the antigen. When the antigen is a peptide, it is, in particular, possible to bind the melanin precursor to the N- or C-terminal of the peptide. It is particularly easy to do so when the melanin precursor is tyrosine or Dopa.

As indicated above, the composition herein disclosed, that is immunogenic, is characterized as being a soluble melanin composition from which the antigen is hardly detectable as a free form in solution, and which is able to induce an immune response against the antigen. It is possible to add free antigens in solution, but the composition as described in the present application is such as it possesses the immunogenic property without such free antigens in solution. In other words, a immune response may be obtained against the antigen even in the absence of free antigen in solution. Thus, a composition containing a melanin macromolecule complexed with an antigen, and an antigen in solution is also within the bounds of the present invention.

One can note that the melanin macromolecule may be disassembled by any method known in the art (such as the one disclosed in Schraermeyer and Dohms, Pigment Cell Res. 1996 October; 9(5):248-54) and that the antigen complexed therein may thus be released, identified and analyzed by any method known in the art such as mass spectrometry.

Polymerization of melanin precursors in the presence of the antigen is performed by methods disclosed in the art.

In particular, the melanin precursor and the antigen may be incubated, with or without buffer, with an enzyme such as phenylalanine hydroxylase, tyrosinase, mushroom tyrosinase, tyrosine hydroxylase, peroxidase, Phenol-oxidase, Dopachrome tautomerase, DHICA oxidase, DHI oxidase. The choice of the enzyme will be made by the person skilled in the art depending on the nature of the precursor present in solution with the antigen before polymerization.

The mixture is also exposed to an oxidizing agent as disclosed above in order to promote the polymerization to melanin. When this polymerization is made in the presence of the antigen, it is postulated that the macromolecule thus formed has entrapped the antigen, and/or that a complex between the antigen and the melanin has been formed. Such complex may or may not comprise covalent links between the antigen and the melanin.

When the charge of the antigen is modified, the characteristics of the complex may also be modified.

Generally speaking, several points may be optimized on an antigen-by-antigen basis. Among others, the person skilled in the art may optimize various parameters such as the ratio of cathecol (melanin precursor)/antigen; the degree of oxidation of the cathecol (in particular by optimization of the type of oxidant, pH, buffer, or length of incubation), or the temperature of reaction.

The immunostimulatory composition as disclosed may also comprise another immunostimulatory molecule, ie an adjuvant as disclosed above.

It is preferred when this adjuvant is selected in the group consisting of TLR3 agonists and TLR9 agonists and in particular when this adjuvant that is further added is chosen among Polyinosinic:polycytidylic acid (poly I:C) and CpG oligonucleotides.

The adjuvant can be added with the antigen before initiation of the polymerization of the melanin precursor. In this case, it is possible that it will also be complexed with the antigen, within the melanin/antigen macromolecule.

Alternatively, the adjuvant may be added to the melanin-antigen complex immunogenic composition after that polymerization has occurred. In this case, it is postulated that the adjuvant is not complexed with the melanin/antigen macromolecule.

Use of the Immunogenic Composition

The invention also relates to the use of melanin or a melanin precursor for the preparation of an immunostimulatory composition, or a vaccine intended to elicit an immune response against an antigen when administered to an animal (as disclosed above, including human being). Alternatively, the immunostimulatory composition can be used in vitro in presence of live cells (for example macrophages, dendritic cells or lymphocytes), to sensitize them before administration (preferably injection) in humans or animal. The resulting composition will thus elicit a immune response against the antigen in the recipient. In particular, U.S. Pat. No. 6,210,662 discloses such principle of forming therapeutic or immunogenic compositions consisting of antigen presenting cells activated by contact with a antigen complex. In the present case, the antigen-melanin complex is the one obtained according to methods described herein.

The melanin precursor is exposed to the antigen and the solution is then submitted to polymerization conditions (exposure to agents such as enzymes or chemicals to induce polymerization) thereby leading to the immunostimulatory composition.

The invention also relates to the use of melanin or of a melanin precursor as an adjuvant to increase or elicit an immune response against a target antigen. This is particularly useful when the target antigen is not, by itself, immunogenic (i.e. no immune response is obtained when the antigen is administered).

The invention also relates to melanin or a melanin precursor as an immunostimulatory molecule. In particular, the melanin or a melanin precursor acts to increase the immune response to an antigen when presented with this antigen. It is to be noted that in vivo administration of the melanin precursor and the antigen may lead to in vivo polymerization of the melanin precursor to melanin and to the formation of the immunostimulatory composition disclosed above. This is particularly true when the melanin precursor and the antigen are associated by electrostatic links, when both have an opposite charge.

The invention also relates to a complex comprising a melanin macromolecule complexed with an antigen as an immunostimulatory composition.

The invention also relates to a complex consisting of a melanin macromolecule complexed with an antigen as an immunostimulatory composition.

The invention also relates to melanin or melanin precursor for its use for increasing or eliciting an immune response against a target antigen.

The invention also relates to an immunostimulatory composition comprising a melanin and a target antigen for its use as a vaccine to protect an animal against a disease implicating (i.e. involving and/or concerning) cells expressing inside the cells, at their surface, or secreting the target antigen or epitopes thereof.

The vaccine may be a prophylactic (i.e. intended to protect the recipient against the development of a disease) or a therapeutic (i.e. intended to help the recipient fight an already present disease) vaccine.

The protected animal has been disclosed above, and may be human being.

The disease is linked to the target antigen used in the immunostimulatory composition. In consequence, the antigen or an epitope thereof is expressed or presented by cells of the animal (or by pathogens) during the course of the disease. The disease thus involves or concerns cells expressing the target antigen.

Such expression may be secretion of the antigen (as an illustration, the antigen may be a bacterial toxin), or surface expression of the antigen or epitope thereof (the antigen may be a surface protein of a virus, or an tumor-specific antigen or epitope thereof expressed at the surface of tumor cells), or presentation of the antigen or epitope thereof at the surface of cells (such as a MHC presentation of an antigen or epitope thereof by the target cell).

The invention also relates to a method for obtaining an immunostimulatory composition comprising the steps of a) Providing a composition containing melanin precursors and an antigen b) inducing polymerization of the melanin precursor so as to form a melanin-antigen complex thereby obtaining an immunostimulatory composition able to elicit an immune response against the antigen when administered to a patient, or when incubated with cells in vitro (this would prime the cells which can then be administered to a patient or an animal).

The antigen used in this method is an antigen against which an immune response is sought in a recipient.

Polymerization is induced as indicated above. It is thus preferably an oxidative polymerization. It is preferably induced in vitro but may also be induced in vivo as indicated above.

In a specific embodiment, the composition of a) also contains an adjuvant. Said adjuvant is other than a melanin precursor, and is preferably a TLR3 or TLR9 agonist, such as an adjuvant selected in the group consisting of poly I:C and CpG-oligonucleotides.

EXAMPLES

Methods

In all examples, epitopes presented by H-2 Kb (mouse MHC I) were used (except in example 18 which is also using a mouse MHC-II epitope).

C57-B16, 5-week old, mice were immunized twice (on day 1 and day 7) with the different formulations combined to a Toll-like Receptor 9 (TLR-9) agonist (10 µg of the CpG-28 oligonucleotide, TAAACGTTATAACGT-TACGACGTCAT (SEQ ID NO: 1)). After 2 immunizations, the CD8+immune response was evaluated on day 14 using a gamma interferon (IFNg)-secretion Elispot assay, after restimulation of total splenocytes with the relevant MHC class-1 epitope (SIINFEKL (SEQ ID NO: 2) for Ovalbumine or KVPRNQDWL (SEQ ID NO: 3) for human gp100)

Example 1—Incubation of Antigen and a Melanin Precursor in Presence of an Oxidant Induces an Immune Response The Ovalbumine epitope (SIINFEKL, SEQ ID NO: 2) alone, or mixed with 10 µg of DOPA, or mixed with DOPA and further incubated for 18 hours in the presence of oxygen to promote oxidation, were used as vaccine preparations. While the epitope alone did not trigger any significant CD8 immune response, the association with DOPA, especially after incubation, was able to induce IFNg spots.

Figure 1:
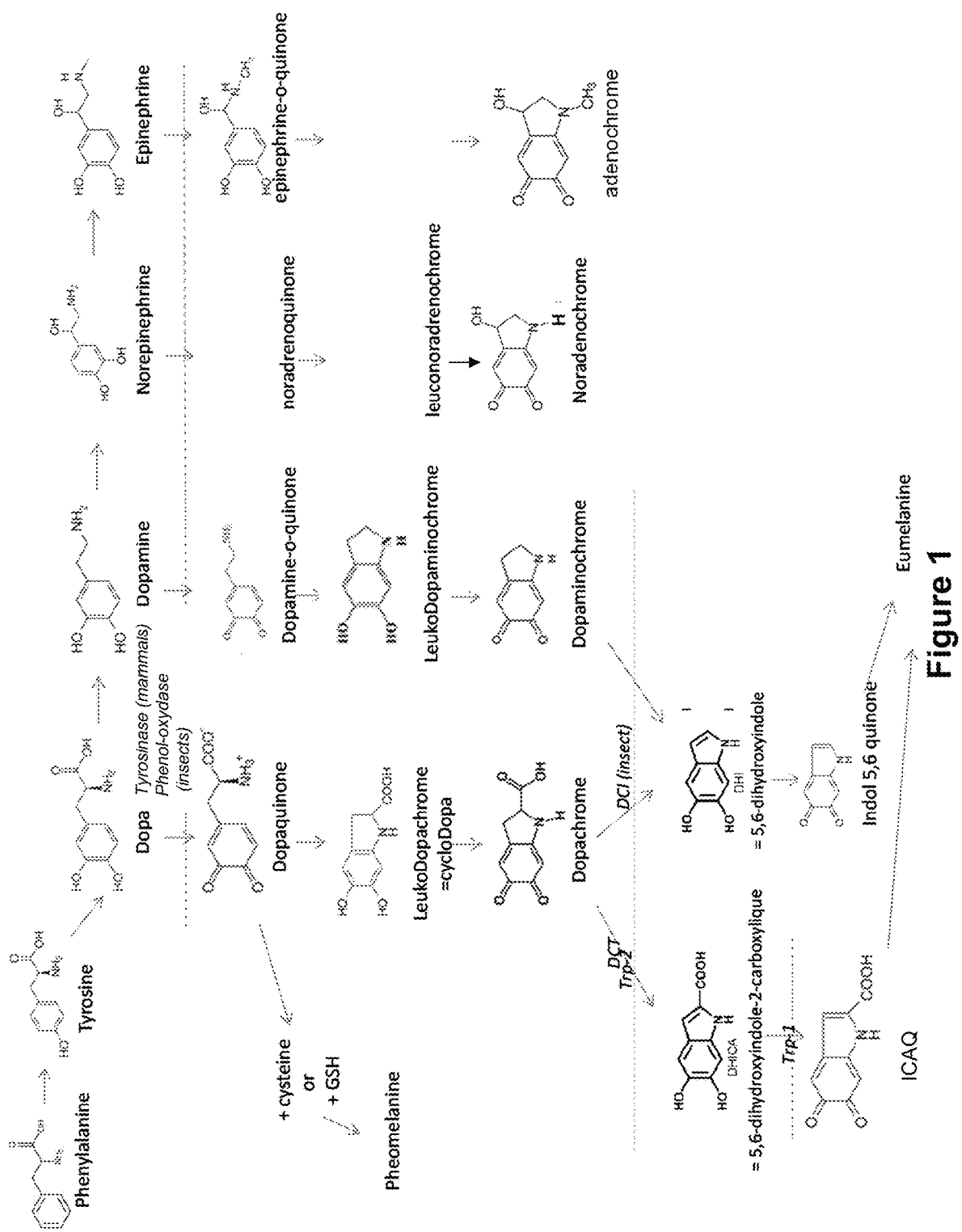
FIG. 1: schematic description of the synthesis of eumelanin starting from phenylalanine.
Figure 2:
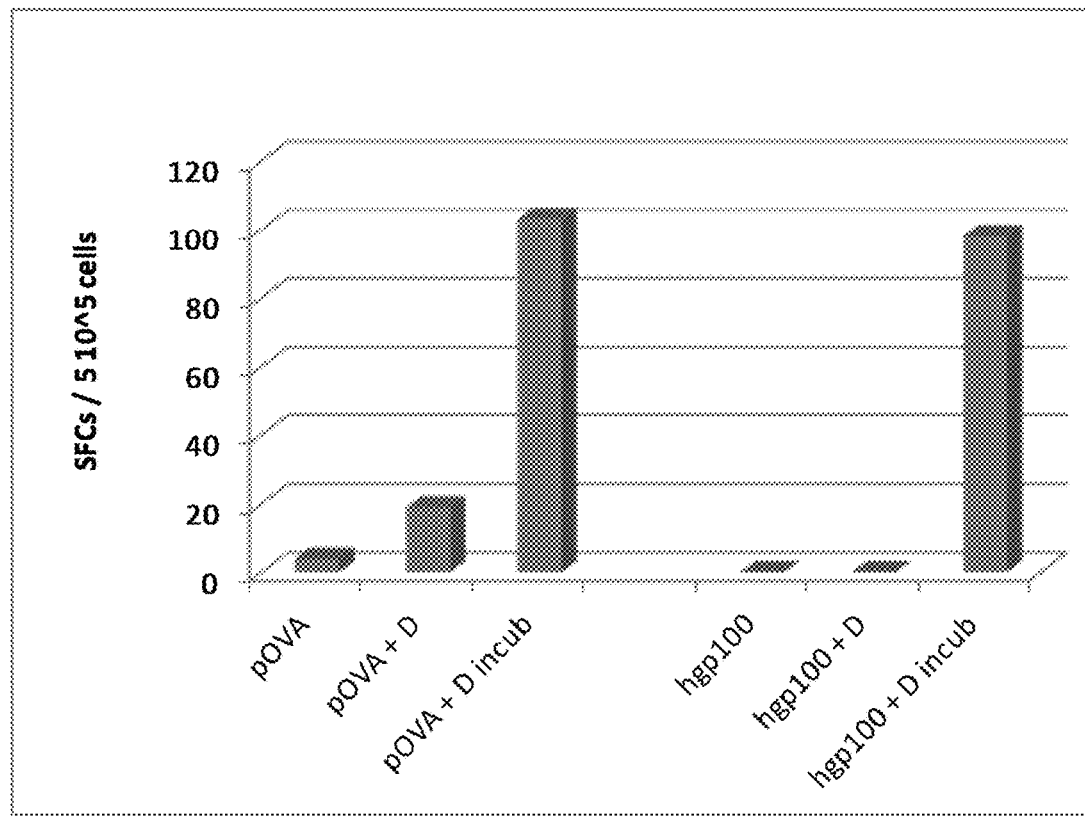
FIG. 2: CTL response after immunization with 1 µg of the Ovalbumine epitope SIINFEKL (pOVA, SEQ ID NO: 2) or 10 µg or the human gp100 epitope KVPRNQDWL (hgp100, SEQ ID NO: 3). C57-B16 mice were injected twice (day 0 & day 7) with the epitope+CpG-28 (SEQ ID NO: 1), the epitope+DOPA (D)+CpG-28; or [the epitope+DOPA, co incubated for 18 hours (D incub)]+10 µg CpG-28 (10 µg Dopa for pOVA; 100 µg Dopa for hgp100). The immune response was assessed on day 14. Splenocytes were re-stimulated in vitro with the corresponding MHC class I-restricted peptide and the numbers of IFNg-SFCs (Spot forming cells) were measured. (Representative experiment with n=4 mice/group).

Similar data were obtained with the poorly immunogenic human gp100 epitope (KVPRNQDWL, SEQ ID NO: 3). Very small amounts of epitope can be used. These results are shown on FIG. 2.

In particular, in this model, as little as 10 ng of SIINEFKL (SEQ ID NO: 2) was sufficient to detect an immune response (data not shown).

Example 2—The Immune Response is not Dependent on the Oxidizing Agent Used (Either Chemical or Enzymatic Oxidation)

Figure 3:
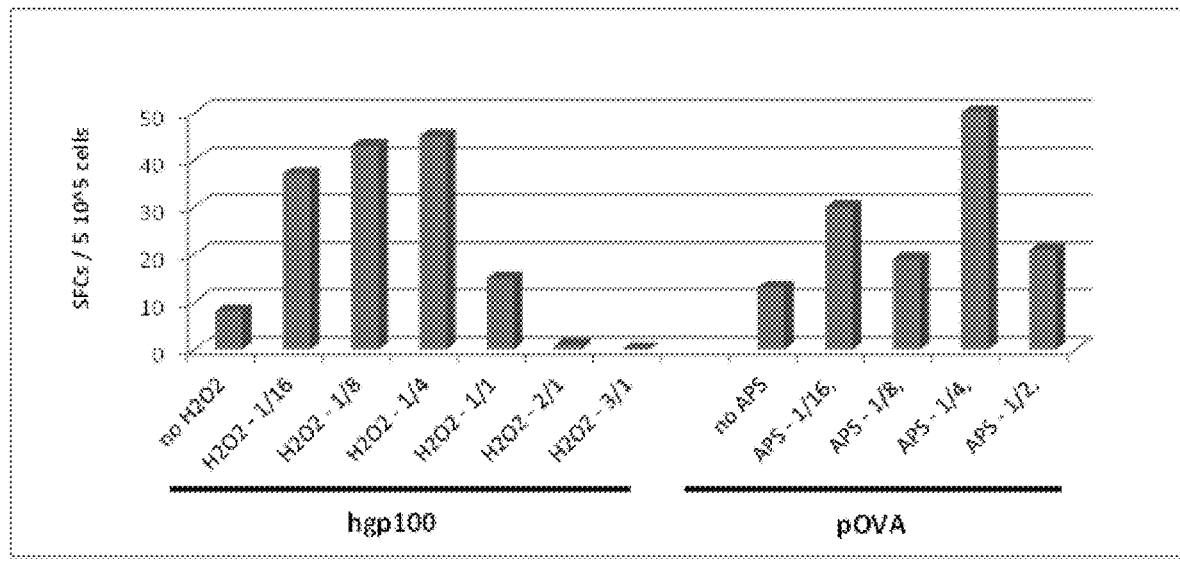
FIG. 3: CTL response after 2 immunizations with 10 µg of peptide KVPRNQDWL (hgp100, SEQ ID NO: 3) or 1 µg SIINFEKL (pOVA, SEQ ID NO: 2), combined with DOPA (100 µg for hgp100, 1 µg for pOVA), and incubated with various molar ratio (oxidant/Dopa) of $H_2O_2$ for 4 hours, or ammonium persulfate (APS) for 2 hours, respectively. In each formulation, 10 µg CpG-28 (SEQ ID NO: 1)/mouse were added before immunizations. The immune response was assessed on day 14. Splenocytes were re-stimulated in vitro with the corresponding MHC class I-restricted peptide and the numbers of IFNg-SFCs (Spot forming cells) were measured. (n=4 mice/group).

Other oxidizing agents such as hydrogen peroxide ($H_2O_2$) or ammonium persulfate (APS) can be used (FIG. 3).

In each case, depending on the antigen and the oxidant used, the optimal concentration is easily defined.

As previously described, a CTL response was seen without addition of any oxidant, but the efficacy of the vaccine was generally enhanced by oxidation, the optimal molar ratio of oxidant/Dopa being around 1/4.

Other oxidizing agents such as ferric chlorure can also be used and lead to the same results.

As shown in Table 1, enzymatic oxidation with mushroom tyrosinase also led to the obtention of a strong immune response.

TABLE 1

| Oxidation procedure | immu-nization protocol | nbr of mice | number of IFNγ-secreting lymphocytes mean +/− SD | negative controls (Irrelevant epitope) mean +/− SD |
|---|---|---|---|---|
| L-Dopa + $Cu^{2+}$ 5 mM ($+O_2$), incubation time: 18 h | day 0 & 8, sacrif day 14 | 4 | 47 +/− 47 | 1 +/− 1 |
| L-Dopa + $Fe^{3+}$ 5 mM ($+O_2$), incubation time: 18 h | day 0 & 8, sacrif day 14 | 4 | 160 +/− 52 | 0 +/− 1 |
| L-Dopa + $Fe^{3+}$ 20 nM ($+O_2$), incubation time: 18 h | day 0 & 8, sacrif day 14 | 4 | 162 +/− 118 | 1 +/− 2 |
| L-Dopa + Mushroom Tyrosinase ($+O_2$), incubation time: 18 h | day 0 & 8, sacrif day 14 | 8 | 246 +/− 164 | 1 +/− 1 |

Example 3—An Immune Response is Observed with Other Melanin Precursor

Figure 4:
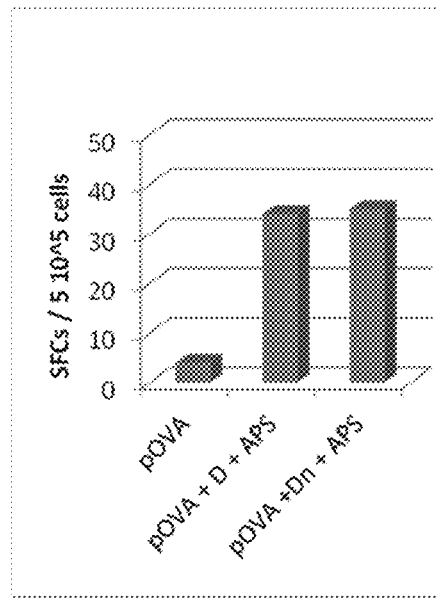
FIG. 4: CTL response after immunization with 1 µg of pOVA (SIINFEKL, SEQ ID NO: 2). C57-B16 mice were injected twice (day 0 & day 7) with peptide+CpG-28 (SEQ ID NO: 1), [peptide+1 µg DOPA+APS] incubated for 4 hours+CpG-28; or [peptide+1 µg Dopamine (Dn)+APS]+CpG-28. The immune response was assessed on day 14. Splenocytes were re-stimulated in vitro with the corresponding MHC class I-restricted epitope SIINFEKL and the numbers of IFNg-SFCs (Spot forming cells) were measured. (Representative experiment with n=4 mice/group).

This example demonstrates that Dopamine can be used instead of DOPA (FIG. 4). In this experiment, 1 µg DOPA or 1 µg Dopamine were mixed to 1 µg SIINFEKL (pOVA, SEQ ID NO: 2), incubated 4 hours with the ammonium persulfate (APS) oxidant and then used as a vaccine preparations in association with 10 µg CpG-28.

Figure 5:
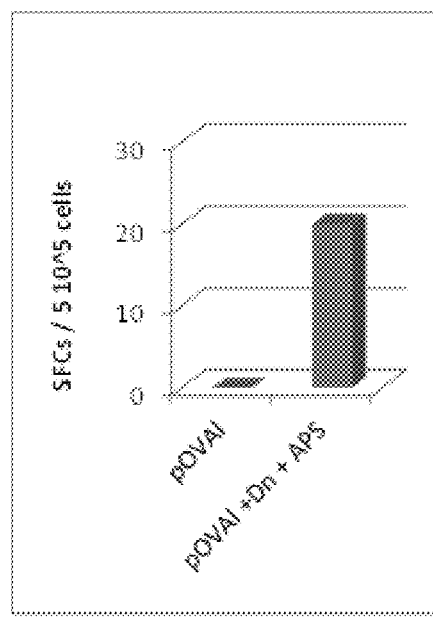
FIG. 5: CTL response after immunization with 3.6 µg or the long OVA peptide (pOVAl, SEQ ID NO: 4). C57-B16 mice were injected twice (day 0 & day 7) with peptide+CpG-28 (SEQ ID NO: 1), or [peptide+100 µg Dopamine (Dn)+APS]+CpG-28. The immune response was assessed on day 14. Splenocytes were re-stimulated in vitro with the corresponding MHC class I-restricted epitope SIINFEKL and the numbers of IFNg-SFCs (Spot forming cells) were measured. (Representative experiment with n=4 mice/ group).

Example 4—Use of a Long Antigen Containing an Epitope Still Makes it Possible to Have the Epitope Processed and Adequately Presented Experiments were conducted to show that other antigens, such as a long peptide, can induce a CTL response with the same procedures. The long OVA peptide (SMLVLLPDEVS-GLEQLESIINFEKLTEWTS (SEQ ID NO: 4)), containing the SIINFEKL epitope (SEQ ID NO: 2), was tested, either alone, or combined to Dopamine and incubated 4 hours with APS and then used as a vaccine preparation in association with 10 µg CpG-28. Only the preparation containing Dopamine triggered an immune response (FIG. 5).

Example 5—Various Adjuvants can be Used in the Composition

In this experiment, it was shown that various adjuvants can be advantageously added to the formulation [Antigen+Dopa].

In this experiment, the used adjuvants were substituted to the CpG-ODN, according to the same protocol than the one disclosed in the Methods above.

The SIINFEKL epitope (SEQ ID NO: 2), was combined (or not) to 100 µg Dopa, further incubated for 18 hours in the presence of oxygen to promote oxidation, and then used as vaccines in association with 10 µg CpG-28 (TLR9 agonist), 10 μg Polyinosinic:polycytidylic acid (poly I:C) (TLR3 agonist), or mixed to Freud adjuvant or aluminium salts (Alum) (vol/vol 1/1).

The CD8 immune response at day 14 was significantly higher for the [DOPA-antigen] composition than the one observed for the antigen without DOPA, especially when the TLR3 or TLR9 ligands were used.

Example 6—The Immune Response Comprises a Humoral Response

Immunization with a composition melanin/antigen induces a humoral response (circulating antibodies).

Ovalbumin protein (1 μg) was mixed to Dopa (1 μg) at pH 7.4, incubated for 4 hours with APS (0.3 μg), and injected subcutaneously with 10 μg in C57/Bml6 mice on day 0 and day 7.

At day 14, significant titers of anti-ovalbumine antibodies of both IgG1 (1/8000) and IgG2b (1/5250) subtypes were seen, showing a mixed Th1 and Th2 immune response.

Example 7—Formation of the Complex Through Co-Incubation is Favourable

It was shown that the co-incubation of the antigen and the catechol moiety during its oxidation makes it possible to potentiate the triggered immunity.

10 μg of the hgp100 epitope (KVPRNQDWL, SEQ ID NO: 3), was either mixed to 100 μg DOPA at pH 8.5, then incubated for 18 hours in the presence of oxygen to promote oxidation, or mixed to a solution of DOPA that has been previously incubated in the presence of oxygen to promote oxidation before the epitope was added.

Figure 6:
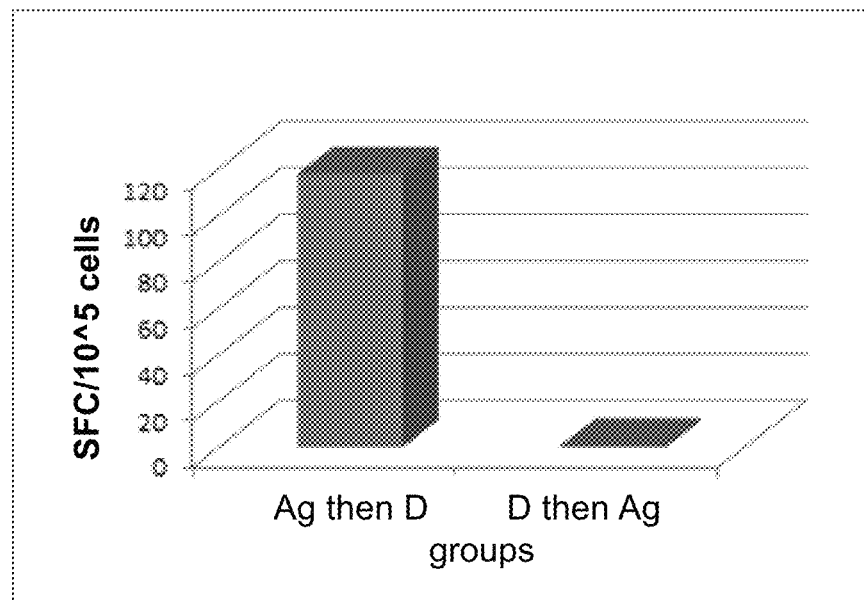
FIG. 6: CTL response after immunization with 10 µg of the human gp100 epitope (hgp100, SEQ ID NO: 3). C57-B16 mice were injected twice (day 0 & day 7) with the epitope co-incubated for 18 hours with 100 µg DOPA at pH 8.5 (Ag then D); or with 100 µg DOPA previously incubated in the presence of oxygen before the epitope was added (D then Ag). In each formulation, 10 µg CpG-28 (SEQ ID NO: 1)/mouse were added before immunizations. The immune response was assessed on day 14. Splenocytes were re-stimulated in vitro with the corresponding MHC class I-restricted peptide and the numbers of IFNg-SFCs (Spot forming cells) were measured. (Representative experiment with n=4 mice/group).

A significant CD8 immune response was seen when the epitope was co-incubated with DOPA (FIG. 6).

Example 8: An Immune Response can be Obtained with Various Melanin Precursor of Derivatives L-Dopa is a convenient catechol to use, leading to soluble melanin. However other melanin precursors can be used. In this experiment, 10 μg of the hgp100 epitope (KVPRNQDWL, SEQ ID NO: 3), were mixed with either 100 μg DOPA,

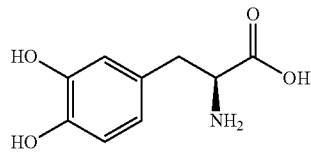 [SMILES: N[C@@H](Cc1ccc(O)c(O)c1)C(=O)O]

100 μg L-Tyrosine,

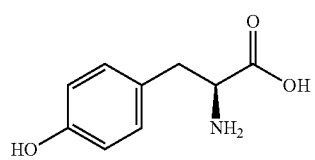 [SMILES: N[C@@H](Cc1ccc(O)cc1)C(=O)O]

100 μg 3-(4-Hydroxyphenyl)propionic acid,

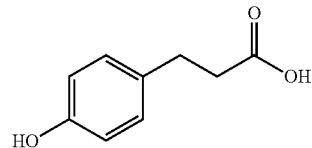 [SMILES: O=C(O)CCc1ccc(O)cc1]

100 μg 6-Hydroxy-DOPA,

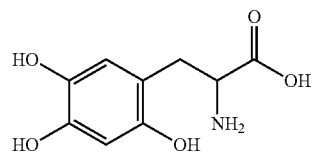 [SMILES: NC(Cc1cc(O)c(O)cc1O)C(=O)O]

100 μg Dihydro caffeic,

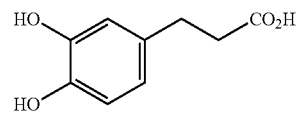 [SMILES: O=C(O)CCc1ccc(O)c(O)c1]

100 μg DHI,

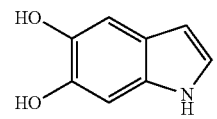

100 μg DHICA,

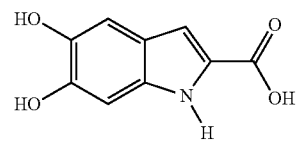 [SMILES: O=C(O)c1cc2cc(O)c(O)cc2[nH]1]

50 μg DHI+50 μg DHICA, or
100 μg HICA,

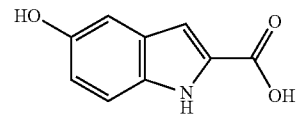 [SMILES: O=C(O)c1cc2cc(O)ccc2[nH]1]

at pH 8.5 in Tris buffer.

The solution was then incubated for 18 hours in the presence of oxygen to promote oxidation.

In each formulations, 10 μg CpG-28/mouse were added before subcutaneous immunizations with various melanin precursors. Mice were either immunized on day 0 & 8 and sacrificed on day 14, or immunized once on day 0 and sacrificed on day 8.

A significant CD8 immune response was seen, especially when the epitope was co-incubated with Dopa (L-Dopa ou D-Dopa), or 6-hydroxydopa, or di-hydroxynaphtalene. Immune responses were also seen, with a reduced magnitude, with Dopamine and Boc-Dopa (N-(tert-Butyloxycarbonyl)-L-dopa).

The presence of an amino-group on the side chain, and of 2 hydroxyl-moieties on the phenolic ring of the melanin precursor appeared very favorable for biological activity and is thus preferred.

Example 9: A Complex is Formed Between the Polymerized Melanin and the Antigen

Figure 8:
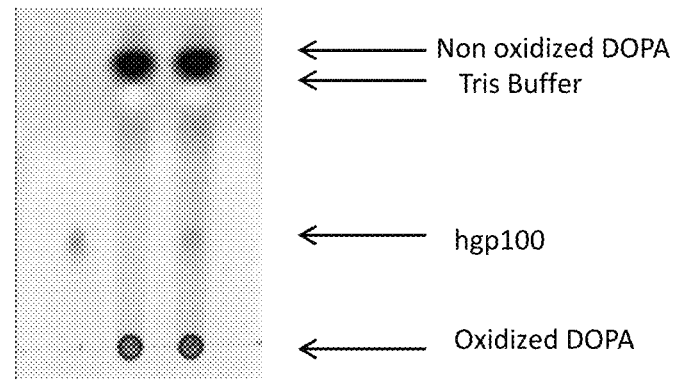
FIG. 8: Thin-layer chromatography (TLC) after a 72-hour incubation at pH 8.5 (Tris buffer). Left: hgp100 (SEQ ID NO: 3). only; middle: hgp100 (1 mg/ml) and Dopa (10 mg/ml), co-incubated with O2; right: hgp100 (1 mg/ml) added after Dopa (10 mg/ml) had been incubated with O2. The peptide, trapped into oxidized DOPA, is not seen any more when both Dopa and the peptide are co-incubated. (TLC was performed on aluminium foils, coated with a thin layer of silica gel as the stationary phase. After the samples have been loaded, a mixture of 1-Butanol/acetic acid/H2O (2/1/1) was used as the mobile phase. The TLC plates were then sprayed with ninhydrin reagent)

In vitro experiments with Thin-layer chromatography (TLC) support the hypothesis that the incubation of the peptide while the catechol is being oxidized modifies the characteristic of the final formulation and that a complex is formed between the two entities (FIG. 8).

Free peptide was seen on TLC only when hgp100 is added after Dopa had been oxidized, but not when Dopa and hgp100 are co-incubated with the oxidizing agent.

It is to be noted that the stability of the peptide in presence of the oxidizing agent was checked and that disparition of the peptide is thus not due to the oxidizing agent.

Figure 9:
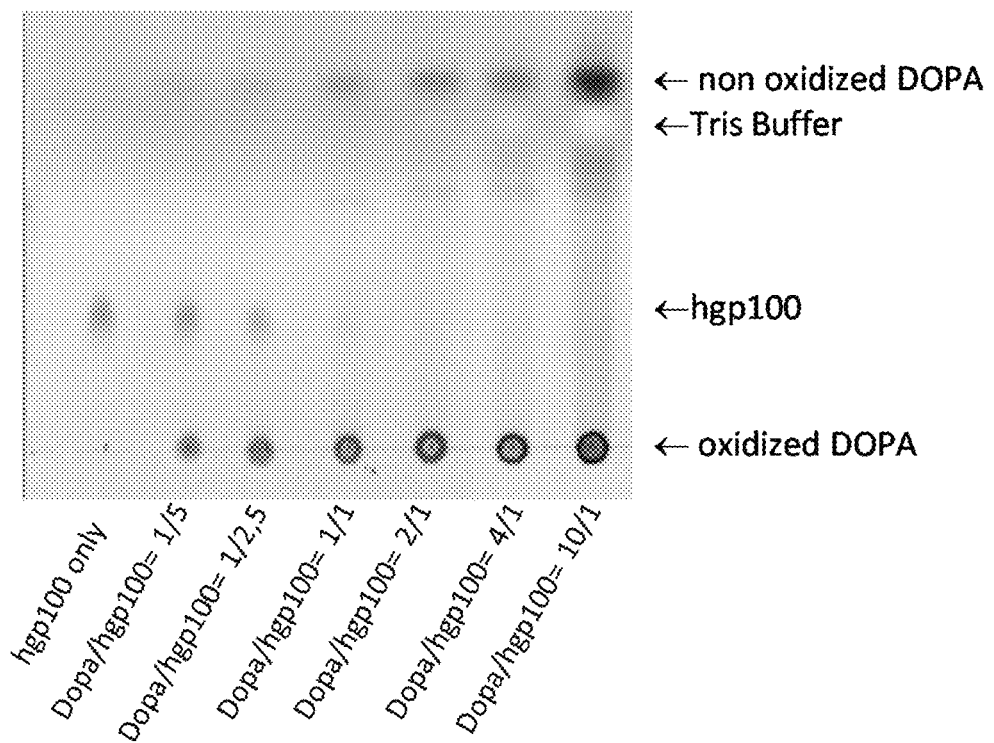
FIG. 9: Thin-layer chromatography (TLC) after a 72-hour incubation at pH 8.5 (Tris buffer). Left: hgp100 (, SEQ ID NO: 3) only; other lanes: hgp100 (1 mg/ml) incubated with various doses of Dopa (Dopa/hgp100 weight ratios: from 1/5 to 10/1). The peptide, complexed with melanin (oxidized DOPA), is not seen any more when the ratio is over 2. (TLC: similar conditions as FIG. 8).

Using Thin-layer chromatography (TLC), it is possible to easily and routinely define the minimal dosage of catechol required for the loading of a certain amount of peptide. For example, with hgp100, a Dopa/peptide weight ration above 2 is favourable (FIG. 9).

Figure 7:
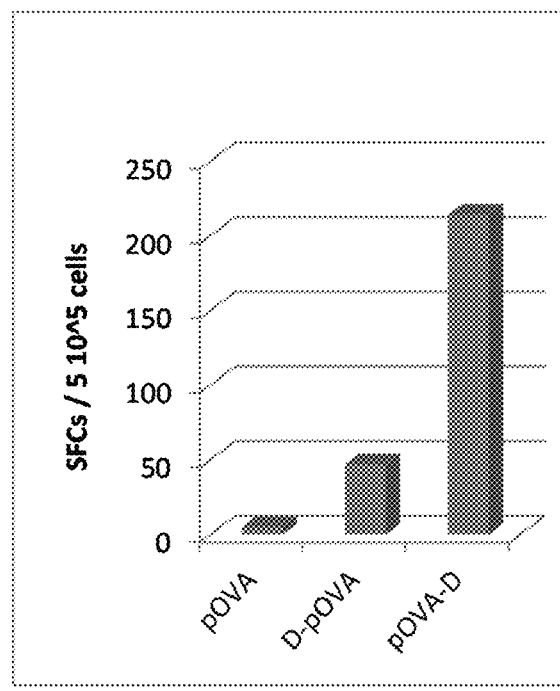
FIG. 7: CTL response after immunization with 1 µg of the Ovalbumine epitope (SIINFEKL=pOVA, SEQ ID NO: 2), or with 1 µg of the epitope synthesized with a DOPA at the beginning (D-pOVA) or at the end (pOVA-D) of the peptide. C57-B16 mice were injected twice (day 0 & day 7) with the peptides+10 µg CpG-28 (SEQ ID NO: 1). The immune response was assessed on day 14. Splenocytes were re-stimulated in vitro with the SIINFEKL (SEQ ID NO: 2) peptide and the numbers of IFNg-SFCs (Spot forming cells) were measured. (n=4 mice/group).

Example 10—An Immune Response is Obtained After Polymerization of DOPA Covalently Linked to the Antigen Mice were immunized either with 1 μg of the Ovalbumine epitope (pOVA, SIINFEKL, SEQ ID NO: 2), or with 1 μg of the epitope synthesized with a DOPA at the beginning (D-SIINFEKL, D-pOVA) or at the end (SIINFEKL-D, pOVA-D) of the peptide. While the epitope alone did not trigger any significant CD8 immune response, the modified peptides, especially the one with a C-terminal DOPA induced strong CTL immune responses (FIG. 7).

Example 11—the Other Adjuvant May be Added Before or after Oxidation

L-DOPA (100 μg) was incubated with the hgp100 epitope (KVPRNQDWL, SEQ ID NO: 3), in presence of the CpG-28 oligonucleotide, then incubated for 18 hours in the presence of oxygen to promote oxidation.

Alternatively, the CpG-28 oligonucleotide was added after oxidation of L-DOPA and the hgp100 epitope.

The immune responses obtained after immunization of the mice with the resulting compositions were similar, thus indicating that the other adjuvant may be added before or after the oxidation (polymerization) reaction.

Example 12—the Complexed Melanin-Antigen Composition May be Obtained as a Soluble Melanin Solution Dopa (2 mg/ml) or Dopamine (2 mg/ml) solutions were incubated with or without the pOVA (0.1 mg/ml) at pH 7.4 or 8.5, and with different oxidizing agents (O2, ammonium persulfate) for 20 hours. All solutions darkened within a few hours. With Dopamine, large aggregates were seen under light microscopy. Under centrifugation, the dopamine solutions precipitated, and some dark material remained adherent to the tubes.

On the contrary, in some conditions (for example when incubated with oxygen at pH8.5), the Dopa solutions did not precipitate, even after centrifugation (16 000 g for 30 minutes) and was not adherent to the tubes. These Dopa solutions remained stable for several weeks, and no aggregates can be seen with light microscopy. This solution can be filtered through a 0.2 μm filter, but not through a 100 kDalton-cut off filter (approx. 0.01 μm).

In conclusion, although both compounds can be successfully used in vaccines formulations, their characteristics differed. Without being bound to this theory, this may be due to a different percentage of DHI and DHICA in each formulation.

Using various percentages of DOPA and Dopamine in the starting composition, (especially according to the antigen characteristics and especially the charge of the antigen) can advantageously lead to various galenic formulations.

Example 13—The Complexed Melanin-Antigen Composition is a Colored Solution

To prepare the formulations, it is preferred when a solution of L-Dopa is mixed with a solution of peptide (weight ratio L-Dopa:epitope between 1:100 and 1:1, preferably between 1:10 and 1:2, depending upon the epitopes), and the mixture is then oxidized at pH 8.5 in aerated conditions.

Figure 12:
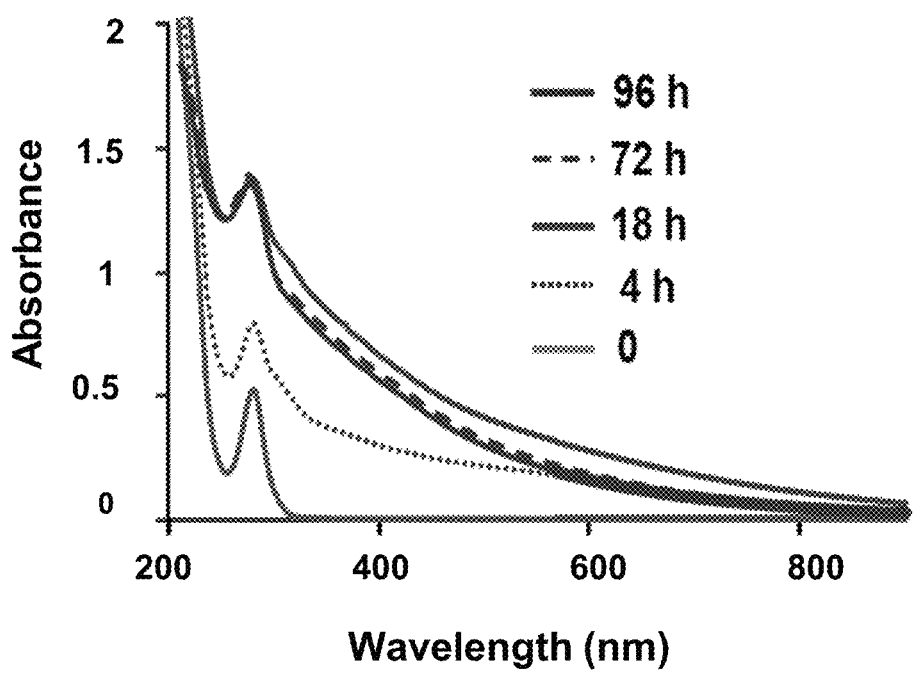
FIG. 12: Physico-chemical characteristics of gp100-bound melanin:UV-visible spectrum (Evolution over time during synthesis). UV visible spectra were obtained using a JASCO V630 spectrophotometer (JASCO, Lisses, France). The solution of polymerizing L-Dopa was diluted 1/20, and spectra were recorded using 1 cm path length quartz cuvette after different incubation times.

Under these conditions, the colorless L-Dopa solution turned black to generate synthetic melanin, a process that can be monitored using UV spectroscopy (FIG. 12). The kinetics of L-Dopa oxidation, can be assessed by the 350/280 nm ratio.

Under these conditions, when filtered through a 10-kDa filter, a black material is retained in the upper chamber, and could be easily resuspended in a saline solution. The resulting product (containing both melanin and peptides) can be further characterized using Fourier transform infrared spectra (FITR), Nuclear Magnetic Resonance (NMR) or Transmission electronic microscopy.

Figure 10:
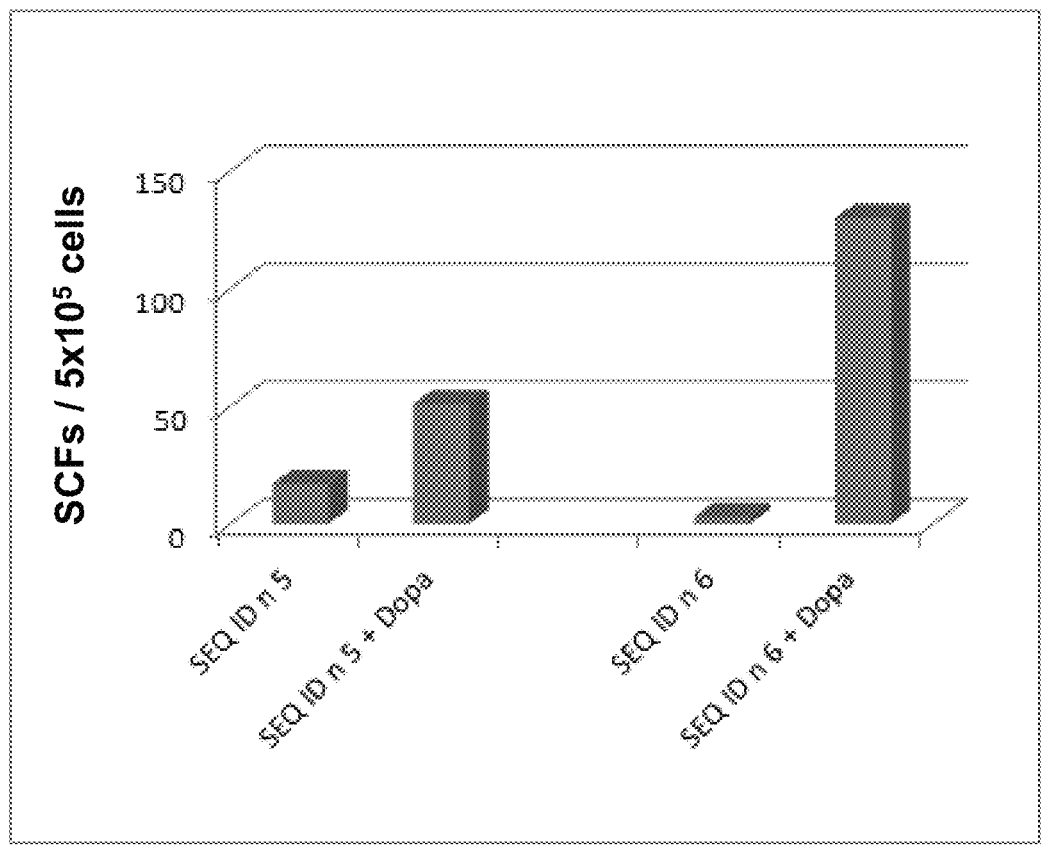
FIG. 10: CTL response after immunization with 3.6 µg of different OVA peptides: SEQ ID NO: 5 (SMLVLLPKSVSGLSQLESIINFEKLTSWTS, neutral), or SEQ ID NO: 6 (SMLVLLPKKVSGLKQLESIINFEKLTKWTS, positively charged). C57-B16 mice were injected twice (day 0 & day 7) with the epitopes co-incubated for 18 hours with 100 µg DOPA at pH 8.5. In each formulation, 10 µg CpG-28 (SEQ ID NO: 1) per mouse were added before immunizations. The immune response was assessed on day 14. Splenocytes were re-stimulated in vitro with the corresponding MHC class 1-restricted epitope SIINFEKL and the numbers of IFNg-SFCs (Spot forming cells) were measured. (n=4 mice/group).

Example 14—Modifying the Antigen Charge can Improve the Immune Response and Immunogenicity of the Composition The charge of the peptide pOVAI (SEQ ID NO: 4) is negative and its sequence was thus modified to make it neutral (SMLVLLPKSVSGLSQLESIINFEKLTSWTS, SEQ ID NO: 5) or positive (SMLVLLPKKVSGLKQLESI-INFEKLTKWTS, SEQ ID NO: 6). When these peptides were used with Dopa (which displays a COO-moiety that is negatively charged) as the melanin precursor, the immune response obtained after 2 immunizations was strong with the positively-charged peptide, and intermediate with the neutral peptide (FIG. 10).

The results obtained after immunization with these peptides and Dopamine (which is positively charged at physiological pH) as the melanin precursor were opposite (i.e. the highest immune response was observed with SEQ ID NO:4 (negatively charged peptide) and the lowest one with SEQ ID NO: 6 (positively charged) whereas the response with SEQ ID NO: 5 was intermediate).

Altogether, these results indicate that it is favourable to modify the antigen in order for its charge not to be the same than the one of the resulting melanin.

Similar data were obtained with the MHC I epitope of Trp2 (VYDFFVWL, SEQ ID NO: 7), which does not contain any positively charged amino-acids.

Adding arginines (R) or lysines (K) to the NH2-terminal end of the peptides enhanced the immune response when compared to unmodified Trp2 (animals were immunized once with formulations consisting of the peptide (10

µg/mouse) co-incubated with L-Dopa (100 µg/mouse), then mixed to CpG-28 (10 µg/mouse). The CD8 immune responses were assessed on day 8).

Similar data were obtained with a viral epitope in Balb/c mice (gPr73: SFAVATTAL, SEQ ID NO: 8). Adding a Lysine at the NH2-terminal end significantly enhanced the immune response. In both cases, if a glutamate (E) was added next to the lysine, the efficacy was reduced (Table 2).

TABLE 2

| epitope structure | nbr of mice | number of IFNγ-secreting lymphocytes mean +/− SD | student-T-test (compared to the native epitope) |
| --- | --- | --- | --- |
| Trp2 | 7 | 30 +/− 34 | / |
| K-Trp2 | 7 | 226 +/− 79 | p < 0.001 |
| R-Trp2 | 7 | 220 +/− 56 | p < 0.001 |
| KAR-Trp2 | 8 | 210 +/− 78 | p < 0.001 |
| KE-Trp2 | 7 | 30 +/− 9 | p = n.s. |
| gPr73 | 8 | 5 +/− 4 | / |
| K-gPr73 | 8 | 21 +/− 16 | p = 0.02 |
| KE-gPr73 | 8 | 14 +/− 22 | p = n.s. |

Example 15—Distribution of Melanin in Draining Lymph Nodes

Ten (10) µg of the hgp100 epitope (KVPRNQDWL, SEQ ID NO: 3) were mixed to 100 µg DOPA at pH 8.5, then incubated for 18 hours in the presence of oxygen to promote oxidation and generate gp100-bound melanin (gp100-melanin).

To assess the distribution of this formulation in vivo, mice were injected subcutaneously with [gp100-melanin+CpG-28] or saline, and sacrificed on days 2 or 7 (n=3/group). To avoid any bias caused by natural melanin, these experiments were carried out in Balb/c mice, which are naturally devoid of melanin. Black pigmentation of the draining inguinal lymph nodes was macroscopically visible on day 2 post-injection in gp100-melanin-injected animals. Fontana-Masson staining confirmed numerous melanin-laden macrophages in the sinuses and, to a lesser extent, in the paracortical areas, which is a T-cell zone. The pattern of melanin distribution was similar at days 2 and 7 post-injection. No melanin was observed in mice that received saline only. These results show that the vaccine formulation effectively reached the draining lymph nodes in vivo.

This finding is consistent with the fact that induction of antigen-specific immunity relies on the direct interaction of DCs with naive T cells that occur in the T-cell zone of lymph nodes.

Example 16—Improvement of the Vaccine Composition

Free gp100 peptide and gp100-melanin were used as vaccine preparations alone or mixed with the TLR9 agonist CpG-28 (CpG) (n=8 mice/group).

Figure 13:
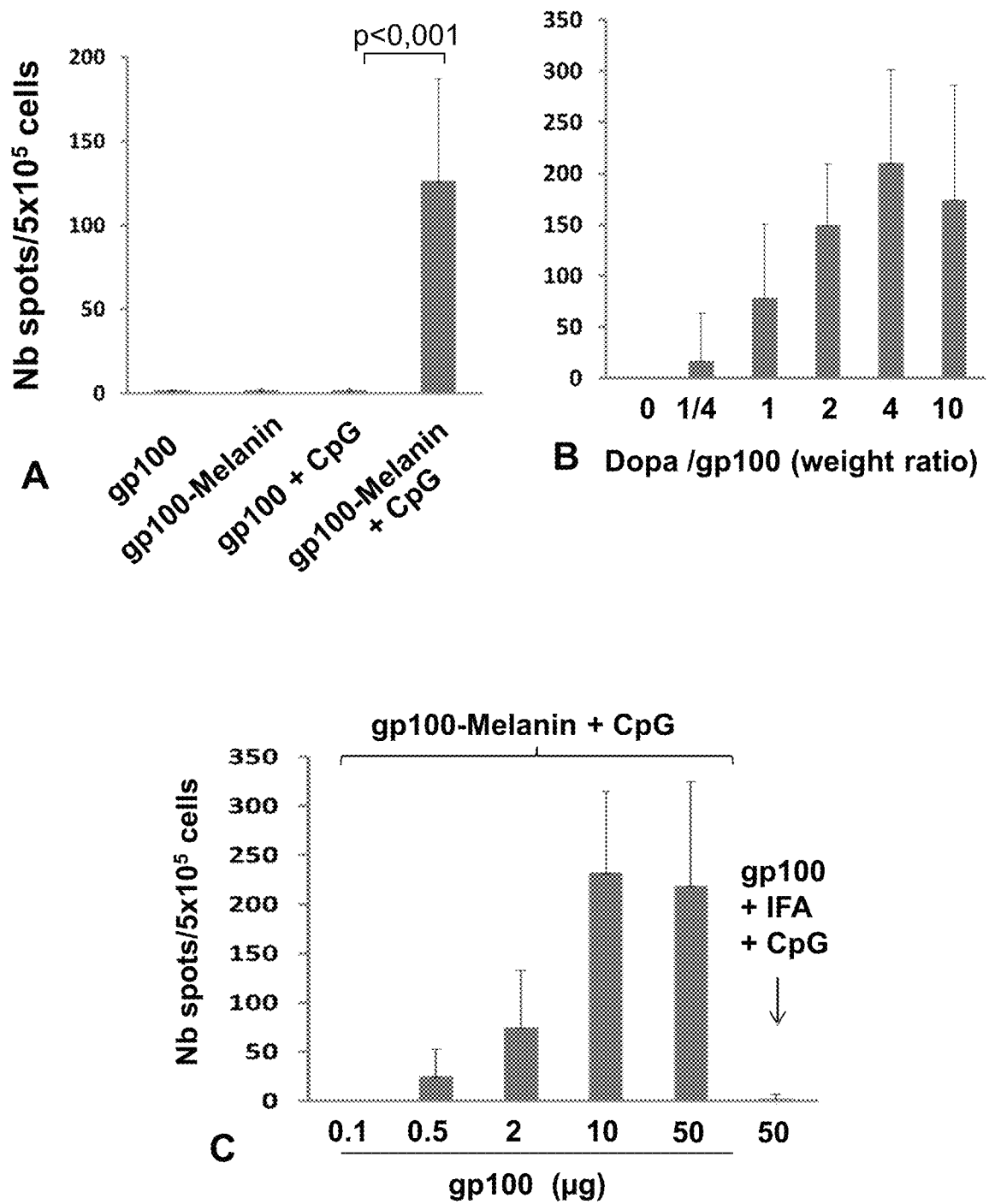
FIG. 13: Numbers of IFNγ-secreting lymphocytes per $10^5$ splenocytes after immunization with various formulations. A. impact of TLR9-agonist in a specific composition with gp100 (SEQ ID NO: 3) and melanin. B. Effect of the ratio of antigen/L-Dopa in the incubation medium to prepare gp100-melanin on the immune response. C. comparison of different gp100-melanin compositions (various antigen dosage) with a composition associating gp100, the classical adjuvant (incomplete Freund's adjuvant, IFA) and a TLR9 agonist.

When combined with CpG, gp100-melanin, but not gp100, induced a significant number of IFNγ-secreting lymphocytes (p<0.001) (FIG. 13A).

If the gp100 epitope was added in the vaccine formulation after L-Dopa had been oxidized instead of before, a reduction in the CTL response was observed (p<0.01).

Significant immunity was obtained with a weight ratio of L-Dopa:epitope starting at 1:1, with the best response observed at a ratio of 4:1 (FIG. 13B). The minimal dose of the gp100 epitope required to induce CTLs was 0.5 µg (p<0.01, when compared to the lowest concentration tested) (FIG. 3c). At both 10 and 50 µg of the gp100 epitope, our vaccine formulation compared favorably (p<0.01) with the combination of incomplete Freund's adjuvant (IFA) and a TLR9 agonist, a combination that is commonly used to trigger CTL responses (FIG. 13C).

Example 17—Complex Melanin-Antigen

Evidence for inclusion of the peptide within melanin was obtained.

A solution of L-Dopa was mixed with an EPHA2 peptide (FSHHNIIRL, SEQ ID NO: 9) at a weight ratio L-Dopa:epitope of 1:4. The mixture was then oxidized at pH 8.5 in aerated conditions.

Figure 11:
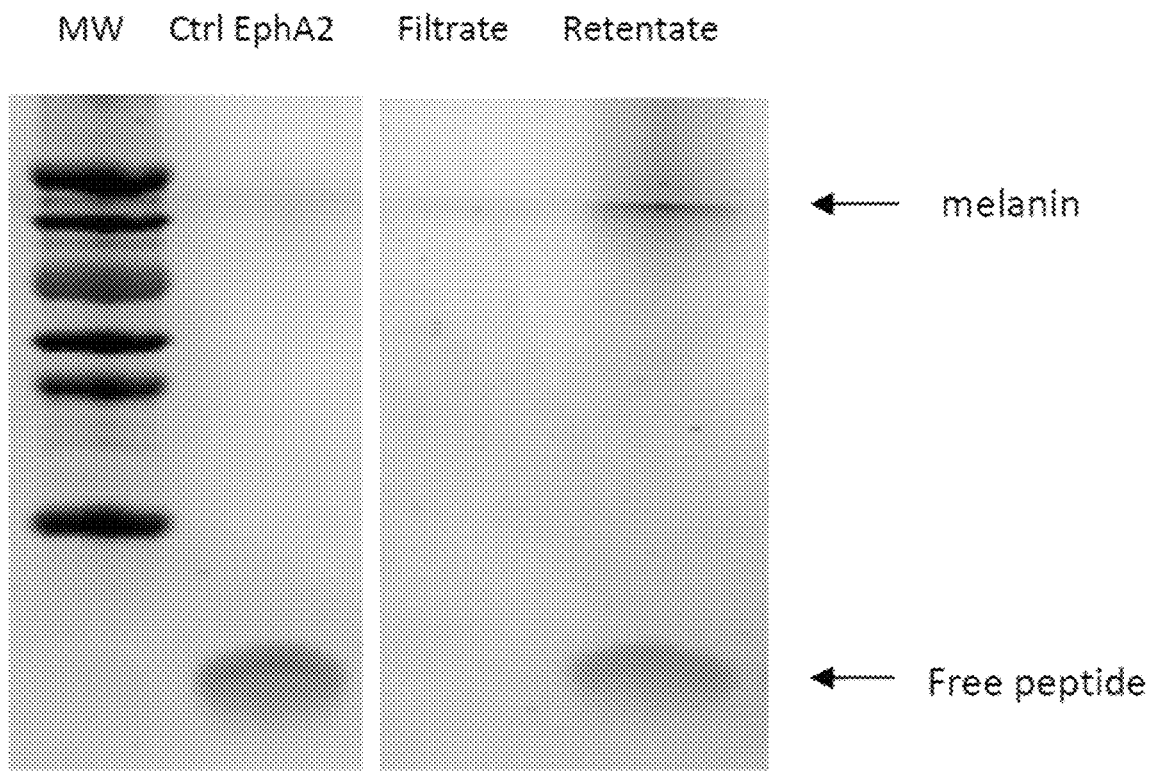
FIG. 11: SDS-PAGE (16% polyacrylamide gel) of various preparations: lane MW: molecular weight marker; lane "Ctrl EphA2": control peptide EphA2 alone (SEQ ID NO: 9); lane "Filtrate": filtrate of complex melanin-EphA2 after filtration on a 10 kD filter; lane "Retentate": retentate of complex melanin-EphA2 after filtration on a 10 kD filter, resuspension, dissolution and heating in loading buffer containing SDS. (Melanin-EphA2 was obtained by co-incubating EphA2 peptide with L-Dopa (weight ration 1:10) in aerated conditions)

When this preparation was filtered on a 10 kD filter, the melanin was retained in the filter and no peptide could detected in the filtrate (FIG. 11, lane Filtrate), suggesting that the EPHA2 peptide was bound to melanin. Indeed, when this retentate was resuspended, dissolved and heated in a loading buffer containing a strong detergent (SDS), the EPHA2 peptide got dissociated from melanin, and can be individualized on SDS-page (16% polyacrylamide gel) (FIG. 11, lane Retentate).

Example 18—Analysis of the Immune Response

The ability of our formulation to trigger a CD4 immune response (MHC class II epitopes) was assessed.

For this purpose, a synthetic peptide (pOVALs) containing both a CD4 (ISQAVHAAHAEINEA, SEQ ID NO: 10) and a CD8 (SIINFEKL, SEQ ID NO: 11) ovalbumine epitopes was synthetized. This peptide bears the sequence SLKISQAVHAAHAEINEAGRLRGSIINFEKLTKWR, SEQ ID NO: 12).

This peptide (10 µg/mouse) was mixed to a solution of L-Dopa (40 µg/mouse), incubated for 18 hours in aerated conditions, to generate pOVAs-melanin, and used as vaccine (without any TLR9 agonist or any further adjuvant).

Mice were immunized either on day 0 & 14 and sacrificed on day 21, or on day 0 & 21 and sacrificed on day 42.

Epitope-specific IFNγ production by splenocytes was determined after in vitro stimulation with the CD4 or the CD8 epitopes.

Figure 14:
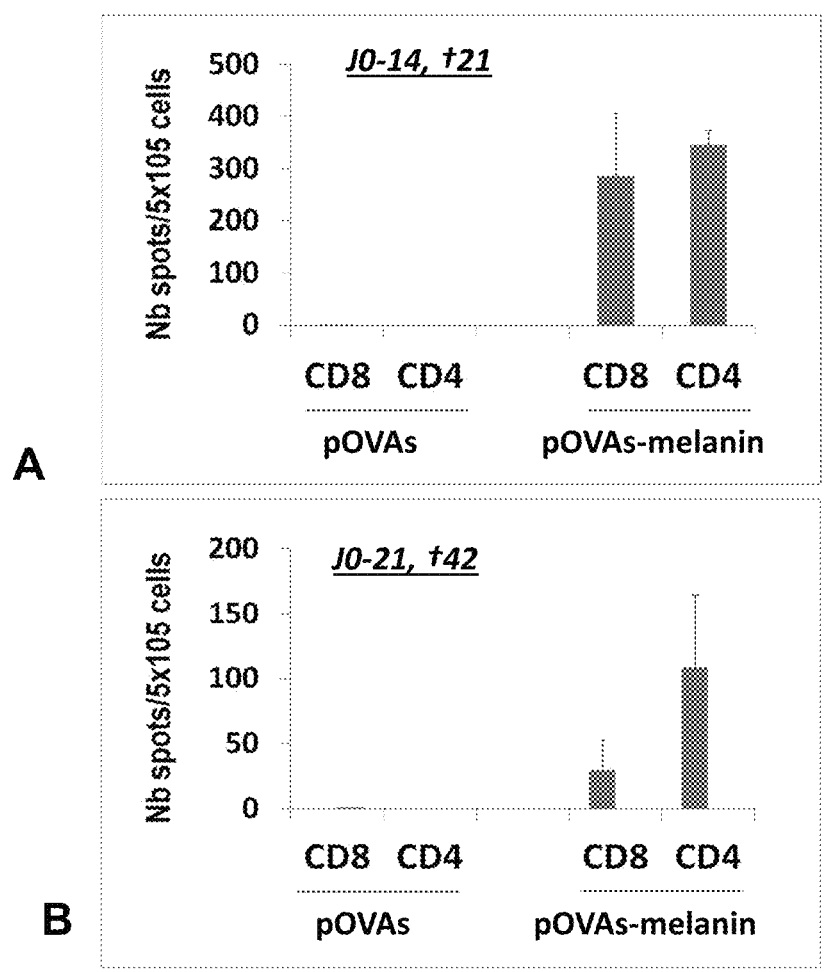
FIG. 14: Number of IFNγ-secreting cells per $10^5$ cells (splenocytes) upon stimulation with a CD4 or CD8 epitope, after immunization of mice with a synthetic peptide (pOV-ALs) (SEQ ID NO: 12).) containing both a CD4 and a CD8 ovalbumine epitopes, either alone or within a composition with melanin. Results shown for mice were immunized on day 0 &14 and sacrificed on day 21 (A), or on day 0 & 21 and sacrificed on day 42 (B).

Formulation with melanin triggered a significant CD4 immune response, in both cases. Moreover, a CD8 immune response was also seen, showing that adjunction of a TLR9 agonist to the formulation is not needed (FIG. 14).

Example 19—Use of Various Adjuvants

The ability of well-described TLR9 agonists, other than CpG-28, to trigger and improve the immune response in mice with the melanin/antigen complex was assessed.

The gp100 peptide (10 µg/mouse) was mixed with L-Dopa (40 µg/mouse), incubated for 18 hours in aerated conditions, mixed with the various TLR9 agonists CpG-28, ODN-1826 (TCCATGACGTTCCTGACGTT, SEQ ID NO: 13, or ISS (TGACTGTGAACGTTCGAGATGA, SEQ ID NO: 14), then used as vaccine preparations.

The magnitude of the immune response was similar for all TLR9 agonists.

TABLE 3

| TLR9 agonist | nbr of mice | number of IFNγ-secreting lymphocytes mean +/− SD | student-T test (compared to CpG-28) |
|---|---|---|---|
| CpG-28 (TLR9 agonist) | 4 | 211 +/− 83 | / |
| 1826 (TLR9 agonist) | 4 | 134 +/− 54 | p = n.s. |
| ISS (TLR9 agonist) | 4 | 147 +/− 63 | p = n.s. |

The efficacy of poly I:C (poly I:C=Polyinosinic:polycytidylic acid), a TLR3 agonist, was also assessed.

C57BL/6 mice were immunized with gp100 (10 μg/mouse)+poly I:C (10 μg/mouse) or gp100 peptide (10 μg/mouse) mixed with L-Dopa (40 μg/mouse), incubated for 18 hours in aerated conditions, and mixed with poly I:C (10 μg/mouse).

Similarly to what was seen with TLR9 agonists, when combined to poly I:C, the melanin formation was superior the free peptide (mean number of IFNγ-secreting lymphocytes +/−SD: 20+/−18 vs 1+/−1, respectively, p=0.02).

Example 20—Subcutaneous Injections of pOVA30-Melanin Protect Against Established Syngenic Tumors It was next investigated whether these CD8+ T-cells were functional in vivo.

Ovalbumin-transfected cells (E.G7-OVA) were injected subcutaneously into C57BL/6 mice, and the mice (n=10/group) were immunized on days 4 and 18 with [melanin+CpG-28], [pOVA30-melanin+CpG-28], [pOVA30+CpG-28]. All of the mice developed measurable tumors.

The pOVA30 peptide (SMLVLLPKKVSGLKQLESIINFEKLTKWTS, SEQ ID NO: 15), contains a CD8 epitope (SIINFEKL, SEQ ID NO: 11) of the ovalbumin protein. pOVA30-melanin was generated by co-incubation of the peptide with L-Dopa in aerated conditions, as described previously.

Figure 15:
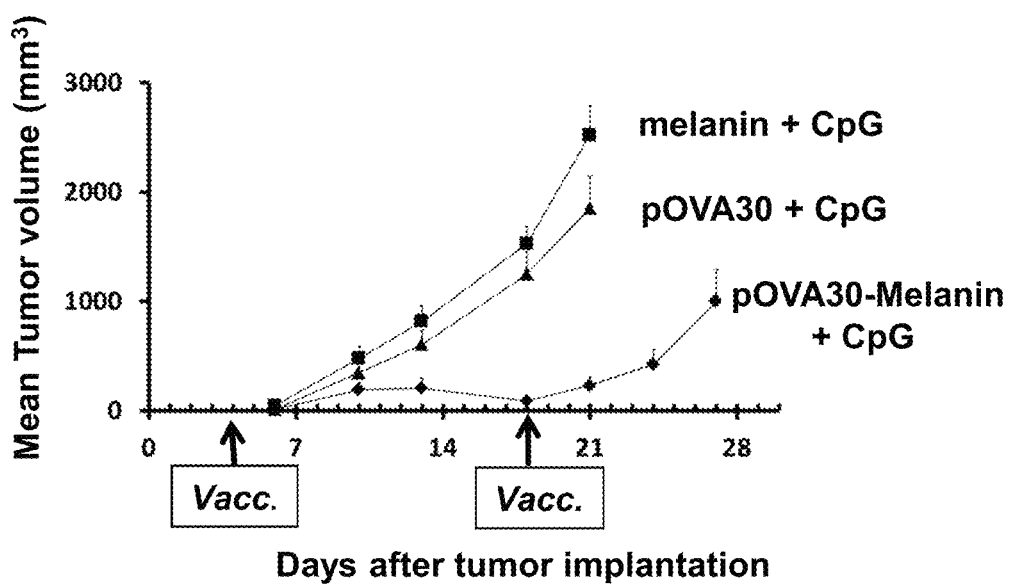
FIG. 15: Mean of tumor volume over time for different vaccine formulations.

A significant decrease in the tumor growth compared with that in the control groups was observed only after immunization with [pOVA30-melanin+CpG-28] (p<0.001) (FIG. 15). Complete tumor regression occurred in 2/10 mice.

Discussion and Comments

The examples above demonstrate that immunization with a complex of a melanin and an antigen makes it possible to obtain an immune response in a host. This immune response is higher than when the antigen is used alone. The immune response may be potentiated when the charge of the antigen and the charge of the melanin precursor, polymerized in the complex, are adapted to each others (preferably when they are not of the same sign).

It is also to be noted that most peptides used in these experiments are containing single MHC epitopes. Consequently, an adjuvant was usually preferred for an optimal immune response to be seen.

However, it was also shown that combining T-helper and MHC class-I epitopes allows the immunogenic compositions according to the invention to induce significant immune responses without the need for an adjuvant, the T-helper epitopes likely allowing recruitment of the T-helper cells and potentiation of the cytotoxic response linked to the MHC class-I epitopes.

The invention claimed is:

1. A method for obtaining an immunostimulatory composition comprising:
 a) providing a composition containing melanin precursor and an antigen,
  wherein the melanin precursor is selected from the group consisting of L-dopa, L-tyrosine, D-dopa, 6-hydroxy-Dopa, dopaquinone, cyclodopa, dopachrome, DHICA, DHI, dopamine-o-quinone, dopamine, leukodopaminochrome, and dopaminochrome; and
 b) inducing oxidative polymerization of the melanin precursor in the presence of an oxidizing agent selected from the group consisting of oxygen, hydrogen peroxide, ammonium persulfate, ferric ions, a combination of sodium iodide and hydrogen peroxide, a salt of a transition metal cation, and a combination thereof;
  thereby obtaining an immunostimulatory composition able to elicit a immune response against the antigen when administered to a subject, or when incubated with cells in vitro.

2. The method of claim 1, wherein the antigen and the melanin precursor in the composition of step a) are covalenty bound.

3. The method of claim 1, wherein the antigen and the melanin precursor in the composition of step a) are not covalenty bound.

4. The method of claim 1, wherein the composition of a) also contains an adjuvant.

5. The method of claim 1, wherein an adjuvant is added to the composition obtained after step b).

6. A method for generating an immune response against an antigen in a subject, comprising administering to the subject an immunostimulatory composition comprising an antigen complexed to a macromolecule, wherein the macromolecule is obtained by oxidative polymerization of a melanin precursor,
 wherein the melanin precursor is selected from the group consisting of L-dopa, L-tyrosine, D-dopa, 6-hydroxy-Dopa, dopaquinone, cyclodopa, dopachrome, DHICA, DHI, dopamine-o-quinone, dopamine, leukodopaminochrome, and dopaminochrome; and
 wherein the oxidative polymerization of the melanin precursor is induced in the presence of an oxidizing agent selected from the group consisting of oxygen, hydrogen peroxide, ammonium persulfate, ferric ions, a combination of sodium iodide and hydrogen peroxide, a salt of a transition metal cation, and a combination thereof.

7. The method of claim 6, wherein the melanin macromolecule is in the form of particles of less than 500 nm.

8. The method of claim 6, wherein the antigen and the melanin precursor were covalently linked prior to polymerization.

9. The method of claim 6, wherein the antigen and the melanin precursor were not covalently linked prior to polymerization.

10. The method of claim 6, wherein the composition also comprises an adjuvant.

11. The method of claim 10, wherein the adjuvant is complexed with the immunostimulatory composition.

12. The method of claim 10, wherein the adjuvant is not complexed with the immunostimulatory composition.

13. The method of claim 10, wherein the adjuvant is selected from the group consisting of alum, emulsions PRR ligands, TLR3 and RLR ligands, TLR4 ligands, TLR5 ligands, TLR7/8 ligands, and TLR9 ligands.

14. The method of claim 6, wherein the antigen comprises at least one epitope selected from the group consisting of MHC epitopes and B-cell epitopes.

15. The method of claim 6, wherein the immune response includes a CD8 T lymphocytes mediated response.

16. The method of claim 6, wherein the immune response includes a CD4 T lymphocytes mediated response.

17. The method of claim 6, wherein the subject is a human being.

* * * * *

SEQUENCE LISTING

```
<160> NUMBER OF SEQ ID NOS: 15

<210> SEQ ID NO 1
<211> LENGTH: 26
<212> TYPE: DNA
<213> ORGANISM: Artificial
<220> FEATURE:
<223> OTHER INFORMATION: CpG-28 oligonucleotide ODN

<400> SEQUENCE: 1
taaacgttat aacgttacga cgtcat                                      26

<210> SEQ ID NO 2
<211> LENGTH: 8
<212> TYPE: PRT
<213> ORGANISM: Artificial
<220> FEATURE:
<223> OTHER INFORMATION: Ovalbumine epitope

<400> SEQUENCE: 2

Ser Ile Ile Asn Phe Glu Lys Leu
1               5

<210> SEQ ID NO 3
<211> LENGTH: 9
<212> TYPE: PRT
<213> ORGANISM: Artificial
<220> FEATURE:
<223> OTHER INFORMATION: human gp100 epitope

<400> SEQUENCE: 3
```

```
Lys Val Pro Arg Asn Gln Asp Trp Leu
1               5

<210> SEQ ID NO 4
<211> LENGTH: 30
<212> TYPE: PRT
<213> ORGANISM: Artificial
<220> FEATURE:
<223> OTHER INFORMATION: long OVA peptide

<400> SEQUENCE: 4

Ser Met Leu Val Leu Leu Pro Asp Glu Val Ser Gly Leu Glu Gln Leu
1               5                   10                  15

Glu Ser Ile Ile Asn Phe Glu Lys Leu Thr Glu Trp Thr Ser
            20                  25                  30

<210> SEQ ID NO 5
<211> LENGTH: 30
<212> TYPE: PRT
<213> ORGANISM: Artificial
<220> FEATURE:
<223> OTHER INFORMATION: neutral long OVA peptide

<400> SEQUENCE: 5

Ser Met Leu Val Leu Leu Pro Lys Ser Val Ser Gly Leu Ser Gln Leu
1               5                   10                  15

Glu Ser Ile Ile Asn Phe Glu Lys Leu Thr Ser Trp Thr Ser
            20                  25                  30

<210> SEQ ID NO 6
<211> LENGTH: 30
<212> TYPE: PRT
<213> ORGANISM: Artificial
<220> FEATURE:
<223> OTHER INFORMATION: positive long OVA peptide

<400> SEQUENCE: 6

Ser Met Leu Val Leu Leu Pro Lys Lys Val Ser Gly Leu Lys Gln Leu
1               5                   10                  15

Glu Ser Ile Ile Asn Phe Glu Lys Leu Thr Lys Trp Thr Ser
            20                  25                  30

<210> SEQ ID NO 7
<211> LENGTH: 8
<212> TYPE: PRT
<213> ORGANISM: Artificial
<220> FEATURE:
<223> OTHER INFORMATION: MHC I epitope of Trp2

<400> SEQUENCE: 7

Val Tyr Asp Phe Phe Val Trp Leu
1               5

<210> SEQ ID NO 8
<211> LENGTH: 9
<212> TYPE: PRT
<213> ORGANISM: Artificial
<220> FEATURE:
<223> OTHER INFORMATION: Viral epitope of gPr73

<400> SEQUENCE: 8

Ser Phe Ala Val Ala Thr Thr Ala Leu
1               5

<210> SEQ ID NO 9
```

```
<211> LENGTH: 9
<212> TYPE: PRT
<213> ORGANISM: Artificial
<220> FEATURE:
<223> OTHER INFORMATION: EphA2 peptide epitope

<400> SEQUENCE: 9

Phe Ser His His Asn Ile Ile Arg Leu
1               5

<210> SEQ ID NO 10
<211> LENGTH: 15
<212> TYPE: PRT
<213> ORGANISM: Artificial
<220> FEATURE:
<223> OTHER INFORMATION: CD4 ovalbumine epitope

<400> SEQUENCE: 10

Ile Ser Gln Ala Val His Ala Ala His Ala Glu Ile Asn Glu Ala
1               5                   10                  15

<210> SEQ ID NO 11
<211> LENGTH: 8
<212> TYPE: PRT
<213> ORGANISM: Artificial
<220> FEATURE:
<223> OTHER INFORMATION: CD8 ovalbumine epitope

<400> SEQUENCE: 11

Ser Ile Ile Asn Phe Glu Lys Leu
1               5

<210> SEQ ID NO 12
<211> LENGTH: 35
<212> TYPE: PRT
<213> ORGANISM: Artificial
<220> FEATURE:
<223> OTHER INFORMATION: Peptide containing CD4 and CD8 ovalbumine
      epitopes

<400> SEQUENCE: 12

Ser Leu Lys Ile Ser Gln Ala Val His Ala Ala His Ala Glu Ile Asn
1               5                   10                  15

Glu Ala Gly Arg Leu Arg Gly Ser Ile Ile Asn Phe Glu Lys Leu Thr
            20                  25                  30

Lys Trp Arg
        35

<210> SEQ ID NO 13
<211> LENGTH: 20
<212> TYPE: DNA
<213> ORGANISM: Artificial
<220> FEATURE:
<223> OTHER INFORMATION: TLR-9 ligand 1826

<400> SEQUENCE: 13
tccatgacgt tcctgacgtt                                           20

<210> SEQ ID NO 14
<211> LENGTH: 22
<212> TYPE: DNA
<213> ORGANISM: Artificial
<220> FEATURE:
<223> OTHER INFORMATION: TLR-9 ligand ISS

<400> SEQUENCE: 14
```

```
tgactgtgaa cgttcgagat ga                                                  22

<210> SEQ ID NO 15
<211> LENGTH: 30
<212> TYPE: PRT
<213> ORGANISM: Artificial
<220> FEATURE:
<223> OTHER INFORMATION: pOVA30 peptide

<400> SEQUENCE: 15

Ser Met Leu Val Leu Leu Pro Lys Lys Val Ser Gly Leu Lys Gln Leu
1               5                  10                  15

Glu Ser Ile Ile Asn Phe Glu Lys Leu Thr Lys Trp Thr Ser
            20                  25                  30
```